(12) United States Patent
Korfhage et al.

(10) Patent No.: US 8,932,831 B2
(45) Date of Patent: Jan. 13, 2015

(54) INSERTION OF SEQUENCE ELEMENTS INTO NUCLEIC ACIDS

(75) Inventors: Christian Korfhage, Langenfeld (DE); Holger Engel, Hilden (DE); Dirk Löffert, Düsseldorf (DE); Ralf Peist, Hilden (DE)

(73) Assignee: Qiagen GmbH, Hilden (DE)

( * ) Notice: Subject to any disclaimer, the term of this patent is extended or adjusted under 35 U.S.C. 154(b) by 3 days.

(21) Appl. No.: 11/744,553

(22) Filed: May 4, 2007

(65) Prior Publication Data

US 2008/0057543 A1 Mar. 6, 2008

(30) Foreign Application Priority Data

May 5, 2006 (DE) .......................... 10 2006 020 885

(51) Int. Cl.
C07H 21/00 (2006.01)
C12Q 1/68 (2006.01)
C12P 19/34 (2006.01)
C12N 15/10 (2006.01)

(52) U.S. Cl.
CPC ................. C12P 19/34 (2013.01); C12N 15/10 (2013.01); C12Q 1/6816 (2013.01)
USPC .......................................... 435/91.2; 536/23.1

(58) Field of Classification Search
None
See application file for complete search history.

(56) References Cited

U.S. PATENT DOCUMENTS

| | | | |
|---|---|---|---|
| 5,545,522 A | 8/1996 | Van Gelder et al. | |
| 5,679,512 A * | 10/1997 | Laney et al. | 435/6.12 |
| 5,962,272 A | 10/1999 | Chenchik et al. | |
| 6,635,425 B2 | 10/2003 | Bandaru | |
| 2003/0104432 A1 * | 6/2003 | Xu et al. | 435/6 |
| 2003/0143599 A1 | 7/2003 | Makarov et al. | |
| 2003/0219751 A1 * | 11/2003 | Lao et al. | 435/6 |
| 2004/0023271 A1 | 2/2004 | Kurn et al. | |

FOREIGN PATENT DOCUMENTS

| | | |
|---|---|---|
| WO | WO00/70095 | 11/2000 |
| WO | WO2004/009814 | 1/2004 |

OTHER PUBLICATIONS

Eberwine et al. (PNAS, 1992, vol. 89, p. 3010-3014).*
Gelder et al. (PNAS, 1990, vol. 87, p. 1663-1667).*
Wharam et al. (Nucleic Acids Research, 2001, vol. 29, No. 11, e54, p. 1-8).*
Myakishev et al. (Genome Research, 2001, vol. 11, p. 163-169).*
Fermentas Thermophilic polymerases (obtained from www.fermentas.com/en/products/all/modifying-enzymes/thermophilic-polymerases Sep. 2010).*
Kapuschoc et al. (RNA, 2002, 8(1):57-66).*
Ryo et al. (Analytical Biochemistry, 2000, vol. 277, p. 160-162).*
Eads et al. (Cancer Research, 1999, vol. 59, p. 2302-2306).*

(Continued)

*Primary Examiner* — Stephanie K Mummert
(74) *Attorney, Agent, or Firm* — Ballard Spahr LLP

(57) ABSTRACT

The present invention concerns a method for inserting one or more tag sequences into a nucleic acid characterized by the following steps: (a) preparation of a template nucleic acid; (b) hybridization of at least one anchor sequence of at least one anchor oligonucleotide with one sequence section of the template nucleic acid; and (c) synthesization of a new strand of nucleic acid, which is partially complementary to the template nucleic acid and which contains a sequence complementary to the non-hybridized portion of the anchor oligonucleotide, e.g. to at least one tag sequence, on its 3' end.

39 Claims, 22 Drawing Sheets

(56) References Cited

OTHER PUBLICATIONS

Patel et al (PNAS, 1996, vol. 93, p. 2969-2974).*
Schramm et al. (Nucleic Acids Research, 2000, 28(22), e96, p. 1-4).*
Huang et al. (Cancer Research, 1997, 57:1030-1034).*
Lizardi et al. (Nature, 1998, p. 225-232).*
deVega et al., *An Invariant Lysine Residue is Involved in Catalysis at the 3'-5' Exonuclease Active Site of Eukaryotic-type DNA Polymerases*, J. Mol. Biol.; vol. 270, No. 1, 65-78, 1997.
Matz M. et al., *Amplification of cDNA ends based on template-switching effect and step-out PCR*, Nucl. Acid Res., vol. 27, No. 6, 1558-1560; (1999).
Okayama H. & Berg P., High-Efficiency Cloning of Full-Length cDNA, Mol. Cell. Biol., vol. 2, No. 2, 161-170 1982.
Wharam S.D. et al., *Specific detection of DNA and RNA targets using a novel isothermal nucleic acid amplification assay based on the formation of a three-way junction structure*, Nucleic Acids Research, vol. 29, No. 11e54, 1-8, (2001).

* cited by examiner

SEQUENCE LISTING

```
<160> NUMBER OF SEQ ID NOS: 23

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Anchor
      oligonucleotide with an 8 base random sequence on
      the 3' end
<220> FEATURE:
<221> NAME/KEY: misc_feature
<222> LOCATION: (0)...(0)
<223> OTHER INFORMATION: n = a, c, g or t

<400> SEQUENCE: 1
aattctaata cgactcacta tagggagaag gnnnnnnnn                               39

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      oligonucleotide with an 8 base random sequence at
      the 3 ' end
<220> FEATURE:
<221> NAME/KEY: misc_feature
<222> LOCATION: (0)...(0)
<223> OTHER INFORMATION: n = a, c, g, or t

<400> SEQUENCE: 2
ggatgacgac gcagtattgn nnnnnnn                                            27

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:
      oligonucleotide with an 10 base random sequence at
      the 3 ' end
<220> FEATURE:
<221> NAME/KEY: misc_feature
<222> LOCATION: (0)...(0)
<223> OTHER INFORMATION: n = a, c, g, or t

<400> SEQUENCE: 3
ggatgacgac gcagtattgn nnnnnnnnn                                          29

<210> SEQ ID NO 4
```

```
<211> LENGTH: 31
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (0)...(0)
<223> OTHER INFORMATION: n = a, c, g, or t

<400> SEQUENCE: 4
ggatgacgac gcagtattgn nnnnnnnnn n                              31

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer
      with with oligonucleotide with an 6 base random
      sequence at the 3' end
<220> FEATURE:
<221> NAME/KEY: misc_feature
<222> LOCATION: (0)...(0)
<223> OTHER INFORMATION: n = a, c, g, or t

<400> SEQUENCE: 5
aattctaata cgactcacta tagg                                     24

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      oligonucleotide with an 6 base random sequence at
      the 3' end
<220> FEATURE:
<221> NAME/KEY: misc_feature
<222> LOCATION: (0)...(0)
<223> OTHER INFORMATION: n = a, c, g, or t

<400> SEQUENCE: 6
ggatgacgac gcagtattgn nnnnn                                    25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: with
      oligonucleotide with an 6 base random sequence at
      the 3' end
<220> FEATURE:
<221> NAME/KEY: misc_feature
<222> LOCATION: (0)...(0)
<223> OTHER INFORMATION: n = a, c, g, or t

<400> SEQUENCE: 7
ggatgacgac gcagtattgn nnnnnt                                   26

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: with
      oligonucleotide with an 6 base random sequence and
      a T base at the 3' end
<220> FEATURE:
<221> NAME/KEY: misc_feature
```

```
<222> LOCATION: (0)...(0)
<223> OTHER INFORMATION: n = a, c, g, or t

<400> SEQUENCE: 8
ggatgacgac gcagtattgn nnnnntt                                        27

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      oligonucleotide with an 6 base random sequence at
      the 3' end
<220> FEATURE:
<221> NAME/KEY: misc_feature
<222> LOCATION: (0)...(0)
<223> OTHER INFORMATION: n = a, c, g, or t

<400> SEQUENCE: 9
ggatgacgac gcagtattgn nnnnttt                                        28

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:
      oligonucleotide with an 6 base random sequence at
      the 3' end

<400> SEQUENCE: 10
aattctaata cgactcacta tagggagaag g                                   31

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      oligonucleotide with an 6 base random sequence at
      the 3' end

<400> SEQUENCE: 11
gtctcaagtc agtgtacagg                                                20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:
      oligonucleotide with an 6 base random sequence at
      the 3' end

<400> SEQUENCE: 12
ggatgacgac gcagtattg                                                 19

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:
      oligonucleotide with an 6 base random sequence at
      the 3' end
<220> FEATURE:
<221> NAME/KEY: misc_feature
<222> LOCATION: (0)...(0)
```

```
<223> OTHER INFORMATION: n = a, c, g, or t

<400> SEQUENCE: 13
ggatgacgac gcagtattgg gnnnnnn                                        27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:
      oligonucleotide with an 6 base random sequence at
      the 3' end
<220> FEATURE:
<221> NAME/KEY: misc_feature
<222> LOCATION: (0)...(0)
<223> OTHER INFORMATION: n = a, c, g, or t

<400> SEQUENCE: 14
ggatgacgac gcagtattgg gggnnnnnn                                      29

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: T 7
      Sequence

<400> SEQUENCE: 15
ggattacgac tcagtattg                                                 19

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
      oligonucleotide with an 6 base random sequence and
      a T base sequence at the 3' end
<220> FEATURE:
<221> NAME/KEY: misc_feature
<222> LOCATION: (0)...(0)
<223> OTHER INFORMATION: n = a, c, g, or t

<400> SEQUENCE: 16
ggattacgac tcagtattgn nnnntttt                                       29

<210> SEQ ID NO 17
<211> LENGTH: 8
<212> TYPE: DNA
<213> ORGANISM: Artificial Sequence
<220> FEATURE:
<223> OTHER INFORMATION: Description of Artificial Sequence: Random
      Primer
<220> FEATURE:
<221> NAME/KEY: misc_feature
<222> LOCATION: (0)...(0)
<223> OTHER INFORMATION: n = a, c, g, or t

<400> SEQUENCE: 17 nnnnnnnn                                                              8

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: B-Actin
```

Primer

<400> SEQUENCE: 18
gtgatagcat tgctttcgtg                                              20

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence:
      oligonucleotide with an 8 base random sequence at
      the 3' end
<220> FEATURE:
<221> NAME/KEY: misc_feature
<222> LOCATION: (0)...(0)
<223> OTHER INFORMATION: n = a, c, g, or t

<400> SEQUENCE: 19
caattctaat acgactcact atagggagaa ggnnnnnnnn                        40

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 20
caattctaat acgactcact atagggagaa gg                                32

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence:
      oligonucleotide with an 8 base random sequence and
      an inverse base G at the 3' end
<220> FEATURE:
<221> NAME/KEY: misc_feature
<222> LOCATION: (0)...(0)
<223> OTHER INFORMATION: n = a, c, g, or t

<400> SEQUENCE: 21
aattctaata cgactcacta tagggagaag gnnnnnnnng                        40

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence:
      oligonucleotide with an 8 base random sequence and
      a G base at the at the 3' end
<220> FEATURE:
<221> NAME/KEY: misc_feature
<222> LOCATION: (0)...(0)
<223> OTHER INFORMATION: n = a, c, g, or t

<400> SEQUENCE: 22
caattctaat acgactcact atagggagaa ggnnnnnnnn g                      41

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence:

```
        oligonucleotide with an 8 base random sequence at
        the 3' end
<220> FEATURE:
<221> NAME/KEY: misc_feature
<222> LOCATION: (0)...(0)
<223> OTHER INFORMATION: n = a, c, g, or t

<400> SEQUENCE: 23
caattctaat acgactcact atagggagaa ggnnnnnnnn g                          41
```

INSERTION OF SEQUENCE ELEMENTS INTO NUCLEIC ACIDS

CROSS-REFERENCE TO RELATED APPLICATIONS

This application claims benefit of German Application DE 102006020885.4 filed May 5, 2006, hereby incorporated herein by reference in its entirety.

FIELD OF INVENTION

The present invention concerns methods for inserting sequence elements (also called tag sequences) into nucleic acids.

BACKGROUND

In order to insert a sequence element (a tag sequence) into an existing nucleic acid, in particular at the 3' end, it was necessary, until now, to carry out a nucleic acid synthesis of the opposite strand of the developing nucleic acid or the ligation of a so-called adaptor/linker. These well known methods are time consuming and laborious. At present, three different methods are known for inserting specific tag sequences at the 3' ends of nucleic acids that are comprised of the common steps that (a) an opposite strand is produced for nucleic acid already synthesized in a polymerase reaction or (b) a second enzymatic reaction is needed in order to attach a tag sequence to a nucleic acid. The following three methods are concerned:

1) Earlier, a template-independent DNA polymerase was used to attach a homopolymer at the 3' end of DNA. A template-independent polymerase, which polymerizes the homopolymer in an independent reaction, is necessary according to this method. This method can thus be extended in that an oligonucleotide containing a sequence, which is complementary to the attached homopolymer, can specifically activate the synthesis of the opposite strand. This method was originally used with cDNA cloning (Okayama H. & Berg P., *High-Efficiency Cloning of Full-Length cDNA*, Mol. Cell. Biol. 1982, 161-170). Nowadays, this method is also used for RNA linear amplification.

2) Furthermore, it is also known to use a so-called "template-switching primer" that inserts a specific tag sequence at the mRNA cap end (Matz M., Shagin D., Bogdanova E., Britanova O., Lukyanov S., Diatchenko L. & Chenchik A., *Amplification of cDNA ends based on template-switching effect and step-out PCR*, Nucl. Acid Res., 1999, Vol. 27, No. 6, 1558-1560; U.S. Pat. No. 5,962,272). This method is directly linked to the property of a certain reverse transcriptase, Rnase H-MMLV, in order to attach cytosine nucleotides template-independently at the RNA cap end. This attachment of nucleotides corresponds to a polymer tailing already described under 1), however carried out here with the reverse transcriptase. The cytosine nucleotides can be used for hybridizing an oligonucleotide having G bases at the 3' end. This method is used in cDNA cloning for example.

3) Finally, the opposite strand can also be activated with a primer which is attached externally. This oligonucleotide primer, for example, can contain a specific sequence (tag sequence) at its 5' end in addition to a random sequence, whereby a tag sequence is inserted at the 5' end in the newly synthesized strand. This form of synthesis utilizes a primer with a tag sequence; however, the synthesis of the opposite strand is necessary in each case in order to insert a complementary sequence to the tag sequence at the 3' end. This method is used, for example, in cDNA cloning or amplification reactions.

Thus, for example, US patent application no. 2003/0143599 by Makarov et al. describes a method for producing a DNA molecule that is subsequently cut into random fragments. Then, a primer with an essentially well known sequence is attached to at least one of the fragments produced in order to produce "primer-linked fragments," which are then amplified. However, in the method according to the aforementioned US patent application, the primer is inserted at the 3' end of the resulting DNA fragment by a so-called "tailing" or an adaptor ligation.

Finally, an article (Wharam S. D., Marsh P., Lloyd J. S., Ray T. D., Mock G. A., Assenberg R., McPhee J. E., Brown P., Weston A. and Cardy D. L. N., *Specific detection of DNA and RNA targets using a novel isothermal nucleic acid amplification assay based on the formation of a three-way junction structure*, Nucleic Acids Research, 2001, Vol. 29, No. 11 e54, 1-8) describes the detection of certain DNA or RNA sequences using oligonucleotides with which, however, no "template switch" takes place. Instead, in this case, an oligonucleotide (called an "extension probe") is extended, which binds both to the target sequence, as well as to the "template probe," so that a y- or t-shaped "three-way junction" is formed.

The problem addressed by the present invention is to provide a new method for inserting sequence elements (tag sequences) into nucleic acids which avoids the complexity of the well known multi-step methods described above and which inserts a tag sequence into a first polymerase reaction without subsequent synthesis of the opposite strand at the 3' end of the newly synthesized nucleic acid. The solution to this problem is a method for inserting a tag sequence or several tag sequences into a nucleic acid and is characterized by the following steps:

(a) provision of a template nucleic acid;
(b) hybridization of at least one anchor sequence of at least one anchor oligonucleotide with at least one sequence fragment of the template nucleic acid and
(c) synthesis of a new strand of nucleic acid, which partially complements the template nucleic acid and which contains a sequence complimentary to the non-hybridized portion of the anchor oligonucleotide i.e. at least one template tag sequence, at its 3' end, whereby a double-stranded region of nucleic acid is formed.

Additional advantageous embodiments, aspects and details of the method according to the invention are found in the patent claims, description, and examples, as well as the figures.

SUMMARY OF THE INVENTION

Disclosed herein are methods for inserting one or more tag sequences into a nucleic acid comprising the following steps:

(a) provision of a template nucleic acid;
(b) hybridization of at least one anchor sequence of at least one anchor oligonucleotide with at least one sequence section of the template nucleic acid.
(c) synthesis of a new strand of nucleic acid, which is partially complementary to the template nucleic acid and which contains a sequence complementary to the non-hybridized portion of the anchor oligonucleotide, e.g. to at least one template tag sequence on its 3' end, whereby a double-stranded region of nucleic acid is formed.

Also disclosed are methods for inserting one or more tag sequences into a nucleic acid comprising the steps outlined above, characterized in that the double-stranded region of nucleic acid produced in Step (c) is further processed in a subsequent Step (d).

Also disclosed are methods for inserting one or more tag sequences into a nucleic acid comprising the steps outlined above, characterized in that at least one anchor sequence of at least one anchor oligonucleotide is located at the 3' region and at least one template tag sequence of at least one anchor oligonucleotide is located in the 5' region of at least one anchor oligonucleotide.

Also disclosed are methods for inserting one or more tag sequences into a nucleic acid comprising the steps outlined above, characterized in that at least one template tag sequence contains at least one functional sequence.

Also disclosed are methods for inserting one or more tag sequences into a nucleic acid comprising the steps outlined above, characterized in that a polymerase with slight or no strand displacement activity is used in Step (c).

Also disclosed are methods for inserting one or more tag sequences into a nucleic acid comprising the steps outlined above, characterized in that Step (c) is performed with a primer, from which the synthesis of the new strand of nucleic acid begins.

Also disclosed are methods for inserting one or more tag sequences into a nucleic acid comprising the steps outlined above, characterized in that the procedure for inserting at least one tag sequence into a nucleic acid functions for the synthesis of RNA.

Also disclosed are methods for inserting one or more tag sequences into a nucleic acid comprising the steps outlined above, characterized in that the method for inserting at least one tag sequence into a nucleic acid serves for the synthesis of DNA.

Also disclosed are methods for inserting one or more tag sequences into a nucleic acid comprising the steps outlined above, characterized in that the method for inserting a tag sequence is used for detecting template nucleic acids.

Also disclosed are methods for inserting one or more tag sequences into a nucleic acid comprising the steps outlined above, characterized in that the procedure for inserting nucleic acids is used for fusing DNA fragments.

Also disclosed are methods for inserting one or more tag sequences into a nucleic acid comprising the steps outlined above, characterized in that methylated DNA sections are selectively amplified.

Also disclosed are procedure according to one or more of the methods described above, characterized in that non-methylated DNA sections are selectively amplified.

Also disclosed are uses of an anchor oligonucleotide in a method according to one or more of the methods described above.

Also disclosed are nucleic acids, which are synthesized in a first-strand synthesis, characterized in that it has a tag sequence at its 3' end, inserted during first-strand synthesis in a template-dependent manner, whereby the sequence complementary to the tag sequence is not a part of the template nucleic acid.

Also disclosed are nucleic acids, which are synthesized in a first-strand synthesis, characterized in that it has a tag sequence at its 3' end, inserted during first-strand synthesis in a template-dependent manner, whereby the sequence complementary to the tag sequence is not a part of the template nucleic acid, characterized in that the tag sequence is inserted at the 3' end by means of an anchor oligonucleotide.

Also disclosed are anchor oligonucleotides having an anchor sequence in the 3' region and a template tag sequence in the 5' region, whereby the anchor sequence is hybridized with a template nucleic acid during the synthesis of the new strand of nucleic acid and the template tag sequence, meanwhile is not hybridized with this template nucleic acid, characterized in that the synthesis of the new strand of nucleic acid, which is complementary to a part of the template nucleic acid and whose synthesis begins 3' of the hybridizing site of the anchor sequence of the anchor oligonucleotide at the template strand, ends by means of a template switch of the polymerase at the 5' end of the template tag sequence of the anchor oligonucleotide.

The present invention concerns a method for inserting sequence elements (a tag sequence or several tag sequences) into a nucleic acid that is characterized by the following steps: (a) provision of a template nucleic acid; (b) hybridization of at least one anchor sequence of at least one anchor oligonucleotide with a sequence section of the template nucleic acid; and (c) synthesis of a new strand of nucleic acid, which partially complements the template nucleic acid and which contains a sequence complementary to the non-hybridized portion of the anchor oligonucleotide (template tag sequence) at its 3' end.

The anchor oligonucleotides used in the method according to the invention contain at least one specific sequence (template tag sequence) in the region of their 5' end, whereby a sequence (tag sequence) complementary to this specific (template tag) sequence is inserted into the newly synthesized strand. The anchor oligonucleotide at the 3' end of this template tag sequence has at least one sequence (anchor sequence) complementary to the template nucleic acid, so that hybridization with the template nucleic acid is possible.

In addition to steps (a)-(c) mentioned above, the method according to the invention also contains an additional Step (d), in which the double strand of nucleic acid produced in Step (c) is processed further. This additional processing can, naturally, be accomplished by one or a combination of several steps in which additional processes are performed. Only a few examples are mentioned here:

1) Separation of the double strand into single strands, which is preferably carried out thermally (i.e. by heating), enzymatically and/or with chemical substances.
2) Ligation of the free ends of nucleic acids by naturally occurring single or double-stranded specific ligases or other ligases, such as ribozymes, chemical ligation, for example with thiophosphate (see U.S. Pat. No. 6,635,425) or ligation with another enzyme suitable for ligation, such as topoisomerase.
3) Processing with nucleases, such as endonucleases or exonucleases, for example, that cut/bind nucleic acid in a sequence-specific or sequence-nonspecific manner,
4) RNA synthesis with or without subsequent translation of the resulting RNA.
5) DNA synthesis, for example, a synthesis of one strand of nucleic acid, which is complementary to at least one portion of the newly synthesized strand of nucleic acid, or the amplification of at least one portion of the template nucleic acid.
6) Nucleic acid—nucleic acid interaction, for example an interaction of the newly synthesized nucleic acid with aptamers or a hybridization of the newly synthesized nucleic acid with another nucleic acid, for instance with one or more specific primers.
7) Binding of one or more proteins to the resulting strand of nucleic acid, for example, by, but not limited to, purification or enrichment of a certain species of nucleic acid by protein binding.

8) Labeling of the newly synthesized strand of nucleic acid or an amplification product thereof.

Additional possibilities of processing a double strand of nucleic acid are well known to the person skilled in the art. It is mandatory that the type of processing be carried out according to the steps necessary in the individual experimental method and, thus, chosen by the person skilled in the art accordingly.

The invention discloses a method by which during nucleic acid synthesis, a sequence element or tag sequence is inserted into the newly synthesized nucleic acid, particularly at the 3' end. Thus, an anchor oligonucleotide is hybridized to a target or template nucleic acid through an anchor sequence. If the polymerase used should encounters the anchor oligonucleotide during nucleic acid synthesis, then further synthesis does not take place along the target nucleic acid but instead along the non-hybridized region of the anchor oligonucleotide (i.e. along the template tag sequence of the anchor oligonucleotide), whereby the tag sequence, a sequence complementary to the template tag sequence, is inserted into the resulting nucleic acid at its 3' end. In the method according to the invention, the template switch takes place in Step (c), i.e. the polymerase used jumps from the target or template nucleic acid to the anchor oligonucleotide. Thus in the method according to the invention polymerases are used that have no or only slight strand displacement activity.

FIG. 1 shows a schematic representation of the insertion of a tag sequence with a DNA polymerase during the synthesis of the new strand of nucleic acid. The anchor oligonucleotide has an anchor sequence (designated by "NNNNNN"). The bases of the anchor sequence hybridize with a corresponding complementary section of the template nucleic acid. The primer serves to start the synthesis of the new nucleic acid. If, in the course of the synthesis, the DNA polymerase comes up against the anchor oligonucleotide, the synthesis of the new strand of nucleic acid to the template tag sequence of the anchor oligonucleotide continues by the template switch, whereby the tag sequence, complementary to the template tag sequence, is inserted into the newly synthesized strand of nucleic acid.

The method according to the invention makes it possible, for the first time, to insert tag sequences of any desired sequence into previously defined or random sequence regions (the anchor sequence of the anchor oligonucleotide can be a random, degenerate or specific sequence) into a nucleic acid even during the first polymerase reaction. In this way the above discussed methods known from the state of the art can be improved such that no additional steps are necessary for insertion of a tag sequence into a nucleic acid. This, in turn, saves time and money.

The method according to the invention can be carried out in which all of the aforementioned steps (a)-(c) or, if necessary, (a)-(d) take place, in each case, consecutively, in a separate reaction vessel. In a further embodiment, steps (a)-(c) or, if necessary, steps (a)-(d) are carried out in their entirety, or two or more of the steps mentioned, in the same reaction vessel, which saves additional time.

The sequence element (the tag sequence) is inserted particularly at the 3' end of the newly synthesized strand of nucleic acid.

In the method according to the invention, deoxyribonucleic acid (DNA), ribonucleic acid (RNA), peptide nucleic acid (PNA) or a mixture thereof can be used as nucleic acid. Nucleic acids can also contain base analogs as long as the method according to the invention is thereby not affected.

The anchor oligonucleotide used in this method preferably has at least one 3' anchor sequence and one or more 5' template tag sequence(s) to the anchor sequence.

The at least one template tag sequence contained in the anchor oligonucleotide in turn preferably contains at least one functional sequence.

The anchor sequence of the anchor oligonucleotide used according to the invention can be specific, degenerate or "random." This sequence preferably contains at least 4 bases in order to ensure adequate hybridization. In particular, the number of bases can lie anywhere between 4 and 50, preferably between 4 and 30 and ideally between 6 and 20.

The synthesis of the new strand of nucleic acid in Step (c) of the method according to the invention occurs preferably with a polymerase having only slight strand displacement activity, and, in the most favorable case, none at all ("strand displacement" indicates the ability of a polymerase to split a double strand of nucleic acid into single strands; see also below). The template switch in the method according to the invention can, in principle, take place more efficiently the lower the strand displacement activity of the polymerase used. However, certain specific embodiments of the method according to the invention can be arranged more effectively through slight strand displacement activity of the polymerase (see below).

The method according to the invention can be used in the context of RNA amplification, signal amplification by means of the so-called "rolling circle" method, DNA amplification, DNA amplification of methylated DNA sections, a method for inserting a restriction site for restriction endonucleases for cloning DNA, a method for inserting a restriction site for restriction endonucleases for producing circular DNA molecules, a method for inserting a restriction site for restriction endonucleases for subsequent ligation to linear, large molecules, a method for detecting nucleic acid, for example in the PCR or RT (reverse transcriptase)-PCR, as well as in real-time PCR or real-time RT-PCR (PCR="polymerase chain reaction"), a method for detecting and/or quantifying a specific nucleic acid, for example, in the PCR or RT-PCR, as well as in real-time PCR or real-time RT-PCR, a method for the fusion of transcriptome or genome fragments or a method for the fusion of transcriptome or genome fragments in whole genome amplification or in whole transcriptome amplification.

DETAILED DESCRIPTION OF THE INVENTION

Definitions and Nomenclature

Figure 1:
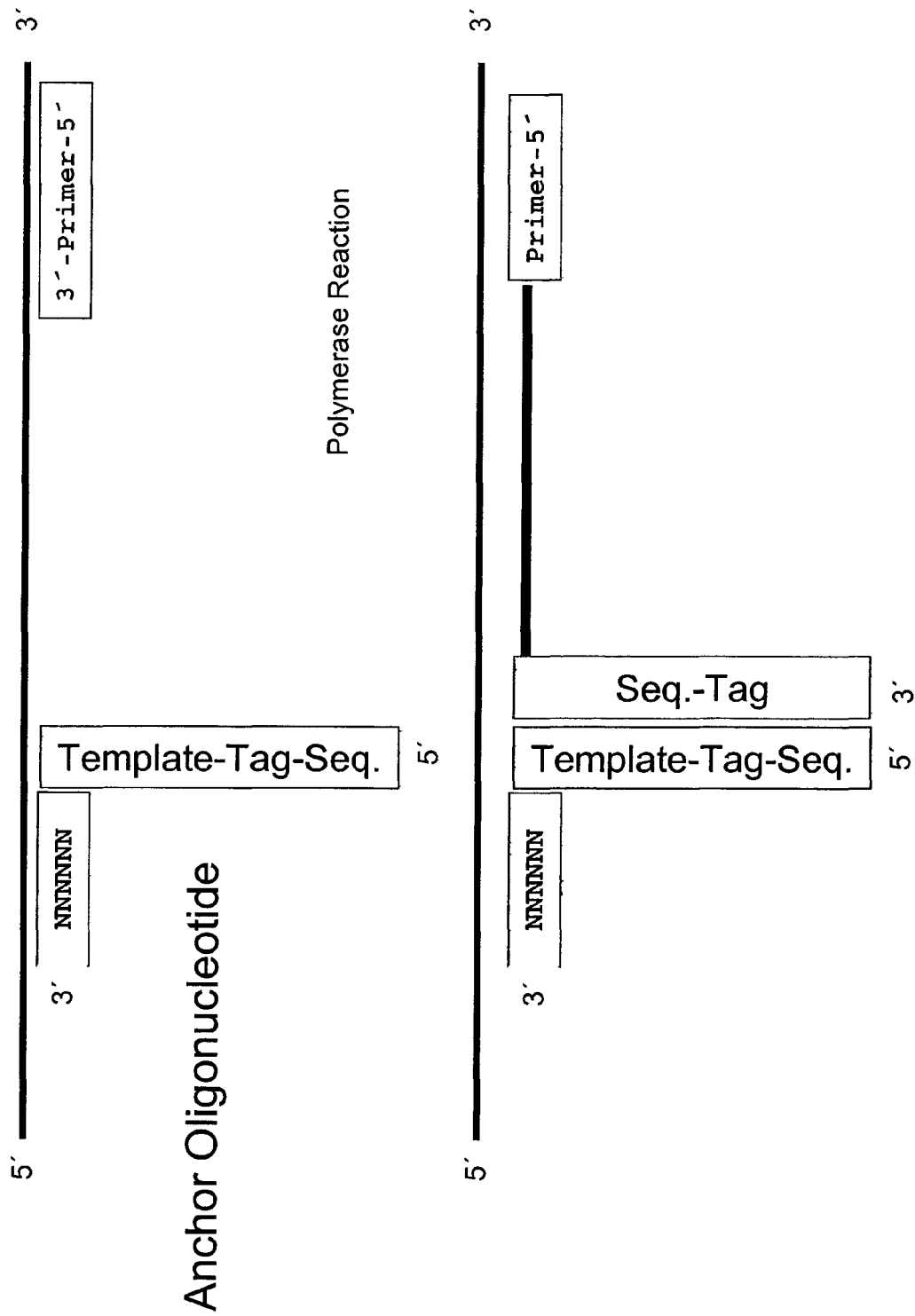
FIG. 1 shows a schematic attachment of a tag sequence by means of the template tag sequence of an anchor oligonucleotide during DNA synthesis with a polymerase.

Some frequently used terms are described in more detail below.

Polymerases

Polymerases are enzymes that catalyze the formation of phosphodiester bonds between individual nucleotides within a strand of nucleic acid (e.g. DNA and RNA polymerases). All polymerases having little or no strand displacement activity under the selected experimental conditions are especially preferred for use in Step (c) according to the method of the invention. In the case that the strand displacement activity is too high, the anchor oligonucleotide could be displaced, which could hinder the insertion of the tag sequence, and, in extreme cases, prevent it completely. Therefore, according to the method of the invention it is most particularly preferred that the polymerases used do not have any strand displacement in the polymerization step. In addition to other polymerases having only slight strand displacement activity, the Klenow fragment of DNA polymerase I, T4 DNA polymerase, T7 DNA polymerase, DNA polymerase I, as well as DNA and RNA-dependent reverse transcriptases belong to these preferred polymerases. Viral, bacterial, archaeobacterial and eukaryotic enzymes belong to the latter, which also include enzymes from introns, retrotransposons and retroviruses, such as MMLV, AMV, HIV, for example. However, other polymerases having only slight strand displacement activity are also suitable for inserting a tag sequence into a developing nucleic acid strand by means of the method according to the invention. Certain specific embodiments of the method according to the invention can be more effectively devised with polymerases with slight strand displacement activity (see below). Moderate strand displacement activity, in the meaning of the present invention, refers to a probability of strand displacement by the polymerase of less than 30%, preferably less than 50% and especially preferably less than 80% of the anchor oligonucleotides. It is well known to the person skilled in the art that the strand displacement probability can vary as a function of reaction temperature, buffering conditions, the respective polymerase and the hybridized fraction of the anchor oligonucleotide.

In the aforementioned sense, heat-unstable polymerases, for example, are suitable for use in Step (c) of the method according to the invention. In principle, all heat-unstable polymerases having no or slight strand displacement activity in the selected experimental conditions, are suitable. DNA polymerases, for example those that effect the repair of a cell's own DNA (called repair polymerases), belong to these heat-unstable polymerases, as well as do replicases. Since replicases frequently have pronounced strand displacement activity, they should be used when their strand displacement activity is low or has been reduced or eliminated through mutation (e.g. Lys143 mutation of the Phi29 DNA polymerase, de Vega et al., An invariant lysine residue is involved in catalysis at the 3'-5' exonuclease active site of eukaryotic-type DNA polymerases; J. Mol. Biol.; 270(1):65-78, 1997), modification or absence of accessory factors. Furthermore, DNA polymerases, such as the Klenow fragment of DNA polymerase I, DNA polymerase I, T4 polymerase, T7 polymerase, as well as reverse transcriptases, belong to these heat-unstable polymerases. In the present invention, a polymerase is termed heat-unstable when it still has a maximal activity of 20% of the initial activity after being treated for 10 minutes at a temperature of 65° C., i.e. when the polymerase has been inactivated to at least 80%.

In addition to heat-unstable polymerases, each heat-stable polymerase in can also be used Step (c) in the method according to the invention. In principle, all heat-stable polymerases having no or slight strand displacement activity in the experimental conditions, are suitable. Accordingly, these polymerases are commercially available and well known to the person skilled in the art. DNA polymerases, for example those that effect the repair of a cell's own DNA (called repair polymerases), belong to these heat-stable polymerases, as do replicases. Since replicases frequently have pronounced strand displacement activity, they should be used when their strand displacement activity is low or has been reduced or eliminated through mutation, modification or absence of accessory factors. Examples of heat-stable polymerases mentioned at this point are the taq polymerase, the Klenow fragment of the taq polymerase and the pfu polymerase, preferably without exonuclease activity (pfu exo).

DNA Polymerases with Strand Displacement Activity

Strand displacement activity of a DNA polymerase means that the enzyme used is able to separate a double strand of DNA into two single strands. Examples of DNA polymerases with strand displacement activity that can be used in RCA are holoenzymes or parts of replicases from viruses, prokaryotes, eukaryotes or archaea, the phi29 DNA polymerases, Klenow DNA polymerase exo⁻ and DNA polymerase from *Bacillus stearothermophilus* designated as Bst exo⁻. "Exo⁻" signifies that the corresponding enzyme does not have 5'-3' exonuclease activity. A well known example of a phi29 DNA polymerase is the bacteriophage phi29 DNA polymerase. Other phi29 polymerases occur, for example, in phages Cp-1, PRD-1, Phi 15, Phi 21, PZE, PZA, Nf, M2Y, B103, SF5, GA-1, Cp-5, Cp-7, PR4, PR5, PR722 and L17. Further suitable DNA polymerases with strand displacement activity are well known to the person skilled in the art. Alternatively, also understood to be DNA polymerases with strand displacement activity are those without strand displacement activity provided a catalyst is used in addition to a respective DNA polymerase, for example a protein or ribosome, which enables a double strand of DNA to be separated or a single strand of DNA to be stabilized. These proteins include, for example, the helicases, SSB proteins and recombinant proteins, which can be present as components of larger enzyme complexes, such as replicases. In this case, a polymerase with strand displacement activity is produced with components in addition to the polymerase itself. The polymerases with strand displacement activity can be either heat-unstable or heat-stable.

Template Nucleic Acids

Examples of template nucleic acids are deoxyribonucleic acid (DNA), ribonucleic acid (RNA), peptide nucleic acid (PNA) or a mixture thereof. A template nucleic acid can also exist in a chemically modified form. They can contain base analogs (e.g. non-purine or non-pyrimidine) or be composed of these, as long as hybridization with a partner strand can take place. Furthermore, the template nucleic acid can also contain other modifications, such as, for example, fluorophore(s), biotin, methylation(s), etc. Alternatively, corresponding modifications are sufficiently known to the person skilled in the art. Necessary properties of a template nucleic acid are that an anchor oligonucleotide can be hybridized to it and that it can be recognized as the target of a polymerase. A template nucleic acid can be of various lengths and be single-stranded, partially double-stranded or double-stranded. In the case of a double-stranded nucleic acid, it must first be denatured in order to allow the hybridization of at least one anchor sequence of the anchor oligonucleotide to take place.

Anchor Oligonucleotides

The anchor oligonucleotide contains at least one specific sequence (template tag sequence) in the region of its 5' end, whereby a sequence (tag sequence) complementary to this specific (tag template) sequence is inserted into the newly synthesized strand. The anchor oligonucleotides have at least one sequence (anchor sequence) on 3' of this template tag sequence complementary to the template nucleic acid, so that hybridization with the template nucleic acid is possible. In addition, one or more sequences which can assume one or more functions can be inserted between the 3' anchor sequence and the 5' template tag sequence. These include, for example, sequences for primer binding sites, probe binding sites, promoters for transcription initiation, restriction endonuclease restriction sites, ribosome binding sites, etc. Any combination of the functions mentioned above is possible in the additional sequence.

Anchor Sequences

The anchor sequence of the anchor oligonucleotide can hybridize to the sequence complementary to the anchor sequence of the template nucleic acid. The anchor sequence can contain a random sequence, a degenerate sequence or a specific sequence and can be of various lengths. Thus, for example, a specific anchor sequence can contain a sequence that can hybridize to the sequence of a transcript, for example, or can partially hybridize to the sequence of the poly-A tail of poly A RNA, or, specifically, to a gene. Moreover, the anchor sequence can also contain functional sequences and, by its nature, can be RNA, DNA or a mixture of both. It can contain base analogs (e.g. non-purine or non-pyrimidine analogs) or nucleotide analogs (for example, PNA) or be composed of both, in so far as hybridization can take place with the target nucleic acid. Furthermore, the anchor sequence can also contain a minor groove binder. Finally, the anchor sequence can contain further modifications, for instance, fluorophore(s), biotin, methylation(s), etc. Corresponding alternative modifications are sufficiently known to the person skilled in the art.

Template Tag Sequence and Tag Sequences

The template tag sequence of the anchor oligonucleotide is the sequence that serves as a template for the tag sequence and which is inserted into the newly synthesized strand of nucleic acid. The template tag sequence can contain a certain sequence. However, the template tag sequence can also contain a degenerate sequence, in so far as this does not hybridize or hybridize poorly to the target nucleic acid. This tag sequence can be of various lengths. Apart from the fact that the tag sequence is inserted into the strand of nucleic acid to be synthesized, it can contain further functional sequences, so that, for example, hybridization sites, primer binding sites, probe binding sites, promoters and signal sequences for transcription and/or translation initiation, restriction endonuclease recognition and restriction sites, ribosome binding sites, protein binding sites, antibody recognition sites, etc. or whose complementary sequences are inserted into the strand of nucleic acid to be synthesized. In addition, the tag sequence can also contain combinations of these functional sequences. The template tag sequence can be, by its nature, RNA, DNA or a mixture of both. The template tag sequence, as well as the tag sequence, can contain base analogs (e.g. non-purine or non-pyrimidine analogs) or nucleotide analogs (e.g. PNA) or be composed of both. The template tag sequence, as well as the tag sequence, can contain further modifications, such as, for example, fluorophore(s), biotin, methylation(s), etc. Corresponding embodiments/modifications are known to the person skilled in the art.

3' End of the Anchor Oligonucleotides

The 3' end of the anchor oligonucleotide can carry a free 3'-OH group; however, the free 3'-OH group can alternatively also be blocked, i.e. the anchor oligonucleotide can no longer be extended at its 3' end with a polymerase, for example. Alternatively, a dideoxynucleotide can also be inserted at the 3' end of the anchor oligonucleotide, so that, in this case, the anchor oligonucleotide can also not be extended, for example, by a polymerase. The 3' end of the anchor oligonucleotide can carry modifications or additions for certain applications. Such additions or modifications can be, for instance, fluorophore(s), biotin, methylation(s), etc. Corresponding embodiments/modifications are known to the person skilled in the art. In the embodiments of the present invention, in which the anchor oligonucleotide functions at the same time as a primer, the 3' end of the anchor oligonucleotide must be extendable by a polymerase, preferably having a 3' OH end.

5' End of the Anchor Oligonucleotides

The 5' end of the anchor oligonucleotide can have a free phosphate group; however, the free phosphate group can alternatively also be blocked or absent. The 5' end of the anchor oligonucleotide can carry modifications or additions for certain applications. Such additions or modifications can be, for instance, fluorophore(s), biotin, methylation(s), etc. Corresponding embodiments/modifications are known to the person skilled in the art.

Rolling Circle Amplification (RCA)

The rolling circle amplification is also known by the name "rolling circle replication." In RCA at least one primer hybridizes to the circular target sequence. With a DNA polymerase with strand displacement activity, the primer is extended and by continuous synthesis at the circular target sequence can be polymerized to a concatemer molecule beyond the primer binding site. The primer used can have a random, degenerate or specific sequence and can be composed of DNA, RNA, PNA, modified bases or base analogs, provided that hybridization with the target sequence and a primer extension can take place with a polymerase. The primer can also be formed through a single strand break in the at least partially double-stranded circular target sequence. Alternatively, DNA polymerases without strand displacement activity can also be used. However, in this case, an enzyme cocktail must be used that contains a catalyst, for example a protein or ribosome, in addition to a suitable DNA polymerase, which enables the separation of a double strand of DNA or the stabilization of a single strand. Helicases, SSB proteins and recombinant proteins belong to these proteins.

Amplification

By nucleic acid amplification, a template increase by at least a factor of 2 or more is meant where the nucleic acid is increased linearly or exponentially. Linear amplification is achieved, for example, by RCA with primers which hybridize with only one specific sequence on the target circle. Exponential amplification is achieved, for example, with RCA with primers, whereby the primers with at least 2 binding sites hybridize on the target circle or hybridize with at least one binding site and at least one binding site on the complementary strand. Other linear and exponential amplification methods appropriate for the present invention are well known to the skilled in the art, for example, PCR, NASBA, SDA, MDA, TMA, 3SR, etc.

Primers

Primer, within the meaning of the present invention, refers to a molecule that functions as a starting point for an enzyme with nucleic acid polymerase activity. This primer can be a protein, nucleic acid or other molecule that demonstrates its suitability as a polymerase starting point to the person skilled in the art. This molecule can function as a starting point through both intermolecular and intramolecular interactions. In the case of nucleic acid primers, these must not hybridize, but, however, can hybridize over their entire length with the template nucleic acid.

First-Strand Synthesis

Within the meaning of the present invention, first-strand synthesis refers to the polymerase-dependent synthesis of nucleic acid in which the newly synthesized strand of nucleic acid is polymerized complementary to a template nucleic acid and whereby a template-dependent tag sequence is inserted at the 3' end of the newly synthesized strand of nucleic acid. With the insertion of the tag sequence, no "tailing" takes place, i.e. no nucleotides are inserted in a template-independent manner into the newly synthesized nucleic acid in the underlying method according to the invention. The template for inserting the tag sequence at the 3' end of the newly synthesized strand of nucleic acid is preferably the template tag sequence of the anchor oligonucleotide which is hybridized to the template nucleic acid by means of its anchor sequence.

Methods

A preferred first embodiment of the method according to the invention concerns the insertion of at least one tag sequence into a nucleic acid during RNA synthesis.

Figure 2:
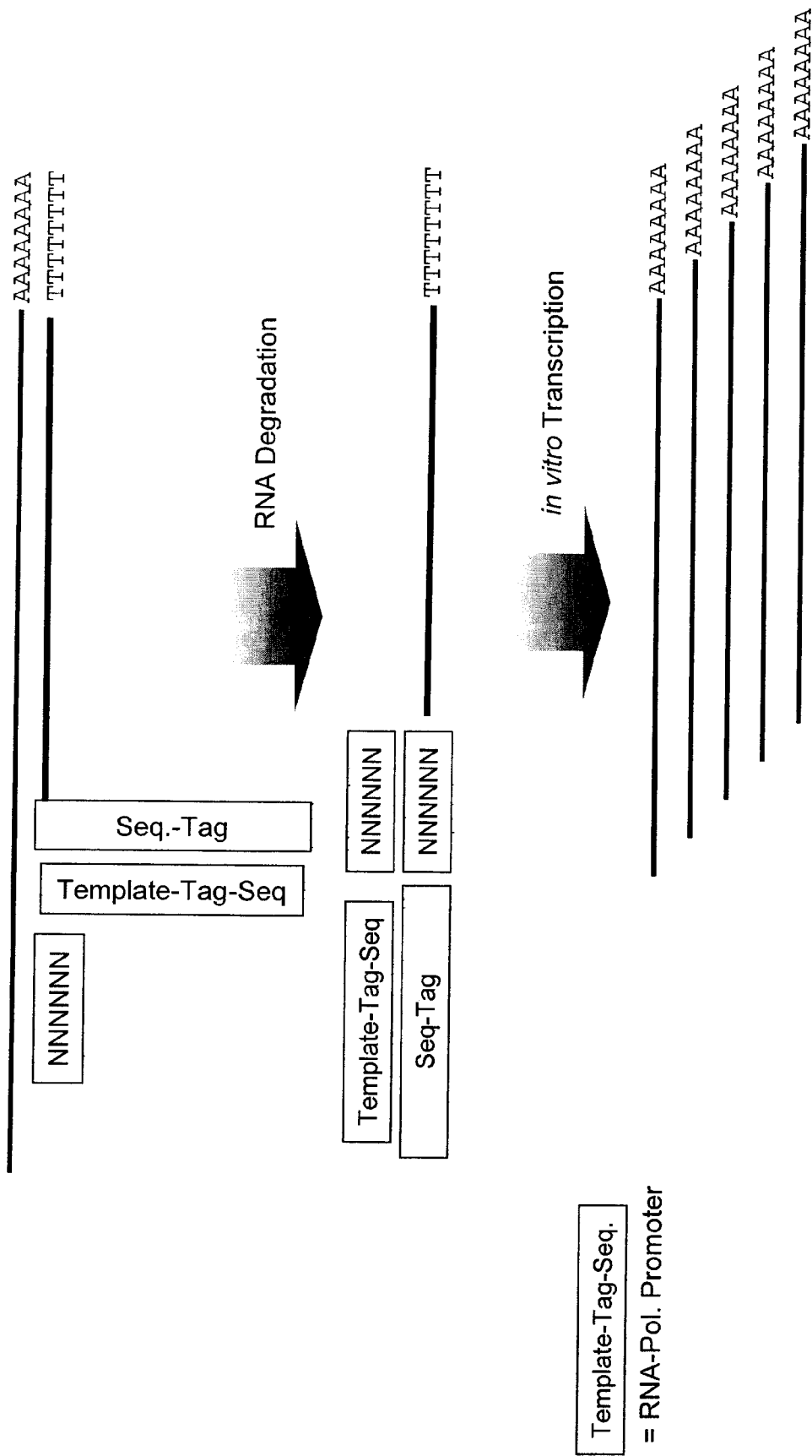
FIG. 2 shows a schematic representation of a method according to the invention in the context of RNA amplification in which a sequence complementary to the promoter sequence is inserted into the newly synthesized strand of nucleic acid by means of a template tag sequence of an anchor oligonucleotide during synthesis of the new strand of nucleic acid.

In principle, RNA amplification methods are described, for example, in U.S. Pat. No. 5,545,522. In this method, an RNA is formed which is oriented in the antisense direction to the starting mRNA. Second-strand cDNA synthesis is unavoidably necessary in this method in order subsequently to arrive at in vitro transcription (amplification) of RNA. However, if an anchor oligonucleotide according to the invention is used, then during first-strand cDNA synthesis of the RNA polymerase, a promoter is already inserted in such a way that, in the following in vitro transcription, the RNA is transliterated in the sense direction without prior second-strand synthesis. A schematic representation of RNA amplification according to invention in which the promoter sequence is inserted by means of the template tag sequence of the anchor oligonucleotide during the synthesis of the new strand of nucleic acid is described in FIG. 2.

According to a preferred implementation of the first embodiment of the method according to the invention, the tag sequence inserted in Step (c) contains at least one RNA polymerase binding site. This RNA polymerase binding site can be, for example, an RNA polymerase promoter.

Furthermore, according to an embodiment of the first embodiment of the method according to the invention, it is preferred that Step (c) is carried out with at least one primer from which synthesis of the new strand of nucleic acid takes place. The inserted primer can be, for example, a nucleic acid, polypeptide or protein. If the primer used is a primer nucleic acid, its sequence can be specific, degenerate or random. An additional advantage can be that the primer used (regardless of whether it is a nucleic acid or a protein) has a tag sequence at the 5' end.

According to a preferred embodiment of the first embodiment of the method according to the invention, the procedure carried out in Step (d), which is an RNA synthesis with an RNA polymerase, takes place in the presence of nucleoside triphosphates (NTPs) and/or modified NTPs.

The strand of nucleic acid, newly-polymerized in Step (c), can then be separated from the template nucleic acid, and this separation can be carried out thermally, enzymatically and/or chemically.

It can also be beneficial if RNA synthesis occurs only after the strand of nucleic acid newly synthesized in Step (c) has been separated from the template nucleic acid.

In a further preferred embodiment of the first embodiment of the method according to the invention, the primer used in Step (c) contains at least one tag sequence. This contains at least one functional sequence, whereby at least one of the functional sequences is an RNA polymerase promoter. Likewise, the template tag sequence of the anchor oligonucleotide has at least one functional sequence, whereby one of the functional sequences is an RNA polymerase promoter. In this embodiment of the method according to the invention the anchor oligonucleotide and primer can be identical. The double-stranded ends produced in Step (c) can now be closed and ligated to each other (for example chemically or enzymatically). Alternatively, these double-stranded ends can be ligated to a self-complementary oligonucleotide. Such a self-complementary oligonucleotide forms a blunt end with itself and can be ligated for example at the double-stranded ends with a ligase. Alternatively, additional functional sequences can be inserted by means of the self-complementary oligonucleotide. AS an alternative to the insertion of an RNA polymerase promoter by means of the template tag sequence of the anchor nucleotide and the primer tag sequence, it can also be inserted by means of the self-complementary oligonucleotide. The length and sequence of such a self-complementary oligonucleotide are dependent on the respective experimental background and can be easily determined by the person skilled in the art. The subsequent synthesis of RNA according to the invention then preferably takes place in the presence of an RNA polymerase and NTPs and/or modified NTPs.

According to a further preferred embodiment of the first embodiment of the method according to the invention, the tag sequence of at least one primer used can be identical with the template tag sequence of the anchor oligonucleotide. The primer tag sequence is preferably at least partially identical to the template tag sequence of the anchor oligonucleotide. Partially identical in the meaning of the present invention means that at least so many nucleotides are identical that the newly synthesized strand of nucleic acid forms a stable double strand at this site under respective experimental conditions. Experience has shown that a sequence with a length of at least ca. 6 nucleotides is necessary. In this case, it is additionally advantageous when after Step (c) strand separation takes place in Step (d), which again, can be carried out thermally, enzymatically and/or chemically.

The tag sequence at the 5' end of the newly synthesized strand of nucleic acid can therefore form a hairpin loop structure at the 3' end through hybridization with the appropriate complementary sequence. The synthesis of RNA, according to the invention, is then preferably carried out in the presence of an RNA polymerase and NTPs and/or modified NTPs.

Both ends of the two hairpin structures can also be ligated. These structures can have blunt ends or also recessed 3' or 5' ends (sticky ends). Alternatively, the two hairpin structures can be joined by sticky end ligation as well as by blunt end ligation. The fact that sticky ends can be converted into blunt ends with a polymerase or exonuclease activity, and therefore easily ligated, is well known to the person skilled in the art. Alternatively, a hairpin structure can be ligated with a self-complementary oligonucleotide. Such an oligonucleotide forms a blunt end and can, for example, be ligated to the hairpin structure using a ligase. Alternatively, additional functional sequences can also be inserted via the self-complementary oligonucleotide. The length and sequence of such a self-complementary oligonucleotide are dependent on the respective experimental background and can easily be determined by the person skilled in the art. The subsequent synthesis of RNA according to the invention, again, is then preferably carried out with an RNA polymerase and NTPs and/or modified NTPs.

The first embodiment of the method according to the invention, can also be used to amplify the hairpin structure formed by using deoxynucleoside triphosphates (dNTPs) and/or modified dNTPs, at least one primer and a DNA polymerase, for example with a DNA polymerase with strand displacement activity, whereby rolling circle amplification takes place. Here, concatemer DNA molecules having hairpin structures are formed. The subsequent RNA synthesis can then take place with an RNA polymerase, NTPs and/or modified NTPs and the DNA templates produced.

According to a further preferred embodiment of the first embodiment of the method according to the invention, the template tag sequence of the anchor oligonucleotide and the primer tag sequence in the 5' direction of the sequence functioning as a RNA polymerase binding site can contain at least one additional functional sequence. At least one additional functional sequence in the template tag sequence of the anchor oligonucleotide, as well as in the primer tag sequence is, preferably, identical. Ideally, the additional functional sequence is a restriction site for a restriction enzyme. The hairpin loop can then be cut at the restriction site with a restriction endonuclease.

The ends of both hairpin structures can then be ligated. These structures can have blunt ends or also recessed 3' or 5' ends (sticky ends). Alternatively, the two hairpin structures can be joined by sticky end ligation, as well as blunt end ligation. The fact that sticky ends can be converted into blunt ends with a polymerase or exonuclease activity, and therefore, easily ligated, is well known to the person skilled in the art. Alternatively, a hairpin structure can be ligated with a self-complementary oligonucleotide. In this case, such an oligonucleotide forms a sticky end and can be ligated to the hairpin structure using a ligase. Alternatively, additional functional sequences can also be inserted by means of the self-complementary oligonucleotide. The length and sequence of such a self-complementary oligonucleotide are dependent on the respective experimental background and can easily be determined by the person skilled in the art. The subsequent synthesis of RNA can then be carried out with an RNA polymerase and NTPs and/or modified NTPs. The hairpin structure formed can be amplified to a DNA template by using deoxynucleoside triphosphates (dNTPs) and/or modified dNTPs, at least one primer and a DNA polymerase with strand displacement activity. Subsequent RNA synthesis can, for example, then take place with an RNA polymerase, NTPs and/or modified NTPs and the DNA templates produced.

According to another preferred embodiment of the first embodiment of the method according to the invention, the primer tag sequence can contain the template tag sequence of the anchor oligonucleotide and, in addition, can have at least one other nucleotide in the 5' direction of this sequence.

According to another preferred embodiment of the first embodiment of the method according to the invention, the template tag sequence of the anchor oligonucleotide can contain the primer tag sequence and, in addition, can have at least one other nucleotide in the 5' direction of this sequence.

If it is still necessary to carry out an additional procedural Step (d) in both of the embodiments mentioned above, then this step would preferably be strand separation that, again, can take place thermally, enzymatically and/or chemically. Strand separation refers to the separation of the double strands into both single strands, whereby the hydrogen bonds between both of the single strands are disrupted.

Furthermore, in both of the embodiments mentioned above, a hairpin structure with an overhang can be formed by hybridizing the tag sequence at the 5' end of the newly synthesized strand of nucleic acid with the appropriate complementary sequence at the 3' end. The ends of both hairpin structures can be ligated. Alternatively, the two hairpin structures can be joined by blunt end ligation. The fact that sticky ends can be converted to blunt ends by polymerase or exonuclease activity, and therefore, easily ligated, is well known to the person skilled in the art. Alternatively, a hairpin structure can be ligated with a self-complementary oligonucleotide. In this case, such an oligonucleotide forms a sticky end and can be ligated to the hairpin structure using a ligase. Alternatively, additional functional sequences can also be inserted by means of the self-complementary oligonucleotide. The length and sequence of such a self-complementary oligonucleotide are dependent on the respective experimental background and can easily be determined by the person skilled in the art. RNA synthesis is then, preferably, carried out with an RNA polymerase and NTPs. The hairpin structure formed can be amplified to a DNA template with dNTPs and/or modified dNTPs, at least one primer and a DNA polymerase with strand displacement activity. Subsequent RNA synthesis can then be carried out with, for example, an RNA polymerase, NTPs and/or modified NTPs and the DNA templates produced.

According to another preferred embodiment of the first embodiment of the method according to the invention, processing takes place after Step (c) in Step (d), in which all newly-produced double-stranded ends are ligated without prior strand separation. This strand separation can subsequently be carried out, for example thermally, enzymatically and/or chemically. Thus, the circular structures produced can be amplified to a DNA template by using dNTPs and/or modified dNTPs, at least one primer and a DNA polymerase with strand displacement activity. Subsequent RNA synthesis is then preferably carried out with an RNA polymerase, NTPs and/or modified NTPs and the DNA template produced.

A preferred second embodiment of the method according to the invention concerns the insertion of at least one tag sequence into a nucleic acid in DNA synthesis.

According to a preferred embodiment of the second embodiment of the method according to the invention, the template tag sequence of the anchor oligonucleotide contains at least one functional sequence complementary to a primer binding site.

A further preferred embodiment proposes that a separation of the newly synthesized strand of nucleic acid from the template strand takes place, if necessary, during processing in Step (d). In addition, DNA synthesis can be carried out with at least one primer, which binds to the primer binding site of the newly synthesized strand of nucleic acid. Finally, it is advantageous if the steps of strand separation and DNA synthesis are repeated several times.

According to a further preferred embodiment of the second embodiment of the method according to the invention, at least one primer for a polymerase reaction is added in Step (c), whereby the primer has a tag sequence containing at least one functional sequence corresponding to a primer binding site. Thus, the template tag sequences of the anchor oligonucleotide and the primer tag sequence can either be identical, partially identical or diverse. Then, if necessary, the newly synthesized strand of nucleic acid can be separated from the template strand for processing in Step (d). According to an additional advantageous embodiment of the method according to the invention, DNA synthesis occurs with at least one primer. The steps of strand separation and DNA synthesis can be repeated several times.

According to further preferred embodiment of the second embodiment of the method according to the invention, the primer with at least one tag sequence used in Step (c) and the anchor oligonucleotide, which are either identical or partially identical, has a template tag sequence. Processing optionally carried out in the following Step (d), is preferably a separation of the newly synthesized strand of DNA from the template strand. This separation can take place thermally, enzymatically and/or chemically. The separated, newly synthesized strand of nucleic acid can form a hairpin structure by self hybridization of the ends. If these hairpin structures have blunt ends, then these ends can ligate two of these structures. The fact that sticky ends can be converted to blunt ends by a polymerase or exonuclease activity and, thus, be easily ligated, is well known to the person skilled in the art. Alternatively, two hairpin structures can be joined by sticky end ligation.

Alternatively, a hairpin structure can be ligated with a self-complementary oligonucleotide. Such an oligonucleotide forms a blunt end and can be ligated to the hairpin structure using a ligase. Alternatively, additional functional sequences can also be inserted with the self-complementary oligonucleotide. The length and sequence of such a self-complementary oligonucleotide are dependent on the respective experimental background and can easily be determined by the person skilled in the art. So, at least one DNA molecule can be produced with a DNA polymerase with strand displacement activity, dNTPs and/or modified dNTPs and at least one primer by means of such a ligated construct. The molecule created in this way can be a concatemer.

According to a preferred embodiment of the second embodiment of the method according to the invention, processing is carried out after Step (c) in an additional Step (d), in which all newly-produced double-stranded ends are ligated without prior strand separation. Strand separation can then be carried out after the corresponding ligation, whereby the resulting strand separation preferably takes place thermally, enzymatically and/or chemically. DNA synthesis can, then again, be carried out with a DNA polymerase with strand displacement activity, dNTPs and/or modified dNTPs and at least one primer.

A further preferred embodiment of the second embodiment of the method according to the invention is that the template tag sequence of the anchor oligonucleotide and the tag sequence of at least one primer used as a functional sequence have a restriction endonuclease binding site in the region of their 5' end. A hairpin structure formed can then be cut on the restriction endonuclease restriction site with a restriction enzyme (a restriction endonuclease), and the ends of the two hairpin structures can be subsequently ligated. The hairpin structures can have blunt ends, as well as recessed 3' or 5' ends (sticky ends). Alternatively, two hairpin structures can be joined by sticky end ligation, as well as by blunt end ligation. The fact that sticky ends can be converted into blunt ends by means of a polymerase or exonuclease activity, and, thus, easily ligated, is well known to the person skilled in the art. Alternatively, a hairpin structure can be ligated with a self-complementary oligonucleotide. In this case, such an oligonucleotide forms a sticky end and can be ligated to the hairpin structure with a ligase. Alternatively, additional functional sequences can also be inserted via the self-complementary oligonucleotide. The length and sequence of such an oligonucleotide are dependent on the respective experimental background and can easily be determined by the person skilled in the art. DNA synthesis then occurs, preferably with a DNA polymerase with strand displacement activity and dNTPs and/or modified dNTPs.

According to a further preferred embodiment of the second embodiment of the method according to the invention, at least one primer is added for a polymerase reaction in Step (c), whereby said primer contains a tag sequence. According to one aspect of this second embodiment, moreover, the template tag sequence of the anchor oligonucleotide can contain the primer tag sequence, and, additionally, at least one other nucleotide in the 5' direction of this sequence. According to another aspect, it is also possible for the primer tag sequence to contain the template tag sequence of the anchor oligonucleotide and, additionally, have at least one other nucleotide in the 5' direction of this sequence. In connection with the two aspects mentioned above, processing in the form of strand separation can be optionally carried out in an additional Step (d), whereby this strand separation preferably takes place thermally, enzymatically and/or chemically. An additional aspect of the method according to the invention is centered on the fact that a hairpin loop structure with an overhang can form by hybridizing the tag sequence at the 5' end of the newly synthesized strand of nucleic acid with the appropriate sequence complementary to the 3' end. The ends of both hairpin structures can then be ligated. It is well known to the person skilled in the art that sticky ends can be converted into blunt ends, which can then easily be ligated by polymerase or exonuclease activity. Alternatively, a hairpin structure can be ligated with a self-complementary oligonucleotide. In this case, such an oligonucleotide forms a sticky end and can be ligated to the hairpin structure using a ligase. As an alternative, additional functional sequences can also be inserted by means of the self-complementary oligonucleotide. The length and sequence of such an oligonucleotide are dependent on the respective experimental background and can be easily determined by the person skilled in the art. Subsequent DNA synthesis is preferably carried out with a DNA polymerase and dNTPs and/or modified dNTPs.

An additional preferred embodiment of the method according to the invention concerns the selective amplification of methylated/non-methylated DNA sections.

In the selective amplification of methylated/non-methylated DNA sections, a tag sequence is inserted at the 3' end of the newly synthesized strand of nucleic acid during a nucleic acid synthesis reaction starting from DNA by means of the template tag sequence of the anchor oligonucleotide. Preferably, at least one primer having a tag sequence is used in Step (c), which is preferably at least partially identical to the template tag sequence of the anchor oligonucleotide. Partially identical, within the meaning of the present invention, means that at least so many nucleotides are identical that the newly synthesized strand of nucleic acid forms a double strand, stable under the respective experimental conditions, at this site. Based on experience, a sequence with a length of at least ca. 6 nucleotides is necessary in order for this to occur.

In the selective amplification of methylated/non-methylated DNA sections, the DNA is cut with methylation-sensitive restriction endonucleases following the nucleic acid synthesis reaction in Step (c). Methylated sites are not recognized by these restriction endonucleases and are, accordingly, not cut. If the methylation-sensitive restriction endonucleases cut hemi-methylated DNA, then, according to the method of the invention, Step (c) must be carried out in the presence of methylated dNTPs, preferably methylated dCTP. The following enzymes, for example, can be used as methylation-sensitive restriction endonucleases: HpaII, AatII, BcnI, Bsh1236I, Bsh1285I, BshTI, Bsp68I, Bsp119I, Bsp143II, Bsu15I, CseI, Cfr10I, Cfr42I, CpoI, Eco47III, Eco52I, Eco72I, Eco88I, Eco105I, EheI, Esp3I, FspAI, HhaI, Hin1I, Hin6I, HpaII, Kpn2I, MbiI, MluI, NotI, NsbI, PauI, PdiI, Pfl23II, Psp1406I, PvuI, SalI, SgsI, SmaI, SmuI, SsiI, TaiI, TauI, XhoI, etc.

During the selective amplification of methylated/non-methylated DNA sections, the DNA can alternatively be cut with methylation-specific restriction endonucleases. By using such endonucleases the non-methylated DNA sections subsequently correspondingly are selectively amplified, after which the newly synthesized strand of nucleic acid is separated from the template strand. The strand separation can be carried out thermally, enzymatically and/or chemically. After strand separation, then, intramolecular hairpin structures can form in the DNA sections not cut, as well as in the methylated regions. As has already been described, these can be used for ligation reactions in order to amplify the nucleic acids in a resulting reaction, for example by rolling circle amplification.

A preferred third embodiment of the method according to the invention concerns the insertion of a tag sequence for detecting template nucleic acids.

According to the third embodiment of the method according to the invention, the template nucleic acid can be, for example, DNA or RNA. Nucleic acid amplification is preferably carried out for detection of the template nucleic acid. Two fundamental aspects can be distinguished in this third embodiment of the method according to the invention. On the one hand, the nucleic acid newly synthesized in Step (c) can be self-amplified in Step (c); on the other hand, the nucleic acid newly synthesized in Step (c) can act as a primer in the amplification of a detection nucleic acid.

If the nucleic acid newly synthesized in Step (c) is amplified for the purposes of detection then, in a first embodiment, the template tag sequence of the anchor oligonucleotide used contains at least one sequence complementary to a primer binding site. In this case, treatment of the nucleic acid construct formed occurs in an additional Step (d), whereby strand separation initially is carried out, preferably thermally, enzymatically and/or chemically. Subsequent to strand separation, amplification of the newly-formed strand of nucleic acid is carried out. The amplification of the newly synthesized nucleic acid is carried out in the presence of at least one primer, whereby its primer binding site is inserted into the newly synthesized strand of nucleic acid by means of the template tag sequence of the anchor oligonucleotide used. With the help of a single primer, the newly synthesized nucleic acid can be amplified, for example, by a linear amplification method. In a further preferred embodiment, at least one further primer complementary to the target nucleic acid can be added in order to enable an exponential amplification of the newly synthesized nucleic acid. This primer can be a nucleic acid, peptide or protein.

In a further preferred embodiment, Step (c) of the third embodiment of the method according to the invention, i.e. during polymerization of the newly synthesized strand of nucleic acid, is carried out in the presence of at least one primer having a tag sequence in its 5' region. This tag sequence primer binds the target nucleic acid with its 3' region, according to the invention, in a region lying 3' from the binding site of the anchor oligonucleotide to the target nucleic acid. The 3' region of the primer can be specific, degenerate or random. According to a preferred aspect, the primer tag sequence contains a sequence complementary to a primer binding site. In further preferred embodiments, the tag sequence can also contain other and/or additional functional sequences. The sequences, contained in the template tag sequence of the anchor oligonucleotide and in the primer tag sequence from Step (c) and complementary to the primer binding site, can be the same or different. With the help of a single primer, the newly synthesized nucleic acid can be amplified, for example, by a linear amplification method. In an additional preferred embodiment, at least one additional primer can be added in order to enable an exponential amplification of the newly synthesized nucleic acid. This at least one additional primer can be a) complementary to the nucleic acid; b) identical with the primer tag sequence; c) completely or partially identical with the part of the primer with a tag sequence from Step (c) which binds to the target nucleic acid; or (d) include the primer fusion site with a tag sequence from Step (c) between the region complementary to the target nucleic acid and tag sequence.

The amplification methods used in the described embodiments of the third embodiment of the method according to the invention can be, for example, polymerase chain reaction ("PCR"), strand displacement amplification (SDA), nucleic acid sequence based amplification (NASBA), self-sustained sequence amplification (3SR), rolling circle amplification (RCA) or multiple displacement amplification (MDA). Further amplification methods applicable to the method according to the invention are well known to the person skilled in the art.

According to a further preferred embodiment of the third embodiment of the method according to the invention, the primer used in Step (c) has a tag sequence, and the anchor oligonucleotide a template tag sequence which is identical or at least partially identical. Treatment that may perhaps be carried out in a subsequent Step (d) is preferably the separation of the newly synthesized DNA strand from the template strand. The separation can be carried out thermally, enzymatically and/or chemically. The separated, newly synthesized strand of nucleic acid can form a hairpin structure by self-hybridization of the ends. If the hairpin structures have blunt ends, two of these hairpin structures can be ligated through their blunt ends. The hairpin structures can also have recessed 3' or 5' ends (sticky ends). Alternatively, two hairpin structures can be joined by sticky end ligation, but also by blunt end ligation. The fact that sticky ends can be converted into blunt ends by polymerase or exonuclease activity which can then be easily ligated is well known to the person skilled in the art. Alternatively, a hairpin structure can be ligated with a self-complementary oligonucleotide. Such an oligonucleotide forms a blunt end and can be ligated to the hairpin structure using a ligase. Alternatively, additional functional sequences can also be inserted by means of the self-complementary oligonucleotide. The length and sequence of such an oligonucleotide are dependent on the respective experimental conditions and can easily be determined by the person skilled in the art. Then, at least one DNA molecule can be produced by rolling circle amplification with such a ligated construct. At least one DNA molecule produced in this way can be a concatemer.

According to a preferred embodiment of the third embodiment of the method according to the invention treatment can be optionally carried out after Step (c) in an additional Step (d) in which all newly-produced double-stranded ends are ligated without prior strand separation. After the corresponding ligation strand separation can be carried out, preferably thermally, enzymatically and/or chemically. Nucleic acid synthesis can once more be carried out by rolling circle amplification.

A further embodiment of the third embodiment of the method according to the invention is that the template tag sequence of the anchor oligonucleotide and the tag sequence of a primer used have a restriction endonuclease restriction site as a functional sequence in the region of their 5' end. A hairpin loop structure formed can then be cut at the restriction endonuclease restriction site with a restriction enzyme (a restriction endonuclease), and the ends of two hairpin structures can be subsequently ligated. The hairpin structures can have blunt ends, or also recessed 3' or 5' ends (sticky ends). Alternatively, two hairpin structures can be joined by sticky end ligation, but also by blunt end ligation. It is well known to the person skilled in the art that sticky ends can be converted into blunt ends, which can then be easily ligated, by polymerase or exonuclease activity. Alternatively, a hairpin structure can be ligated with a self-complementary oligonucleotide. In this case, such a self-complementary oligonucleotide itself forms a sticky end and can be ligated to the hairpin structure with a ligase. Alternatively, additional functional sequences can also be inserted via the self-complementary oligonucleotide. The length and sequence of such a self-complementary oligonucleotide are dependent on the respective experimental background and can easily be determined by the person skilled in the art. DNA synthesis is then carried out, preferably by rolling circle amplification.

According to further preferred embodiment of the third embodiment of the process proposed by the invention, the at least one primer used in Step (c) has a tag sequence and the anchor oligonucleotide a template tag sequence, which are identical in a sub-region and whereby either the template tag sequence of the anchor oligonucleotide or the primer tag sequence from Step (c) has an additional sequence at their 5' ends, whereby this sequence contains an alternating sequence, for example of G-C or A-T bases. In this way, during self-hybridization, a hairpin loop with a so-called sticky end is formed after strand separation. In any case, however, the additional sequence is arranged in such a way that the sticky ends of both newly synthesized strands can hybridize with each other. Appropriate sequences are well known to the person skilled in the art. A treatment potentially carried out in a subsequent Step (d) is preferably a separation of the newly synthesized DNA strands from the template strand. This strand separation can be carried out thermally, enzymatically and/or chemically. The resulting sticky ends are ligated with a ligase. At least one DNA molecule can then be produced by means of such a ligated construct by rolling circle amplification. At least one DNA molecule produced in this way can be a concatemer.

Detecting the nucleic acid formed can take place by means of suitable methods well known to the person skilled in the art. These known methods include, for example, fluorescence detection by means of fluorescence probes or by means of fluorescent, nucleic acid-binding substances, for example, SYBR Green®, ethidium bromide, PicoGreen®, RiboGreen®, etc. The nucleotides employed, for example, in amplification can also be labeled with fluorophores in fluorescence detection. Detecting fluorescence signals and/or the size of the nucleic acid sections produced can be carried out, for example, by gel electrophoresis, capillary electrophoresis, arrays, fluorescence detection devices or a real time-cycler. Detecting nucleic acid can also be carried out by means of its length-dependent mass. In principle, all methods for amplifying a nucleic acid according to the invention can also be used for detecting the amplified nucleic acid, whereby the detection takes place during or after the amplification.

According to a further preferred aspect of the third embodiment of the method according to the invention, the template tag sequence of the anchor oligonucleotide and/or the primer tag sequence from Step (c) contains at least an additional sequence which enables the binding of a nucleic acid probe. Suitable detection probes can be binded to the probe binding sites inserted in such a way. In addition, all probes known to the person skilled in the art for detecting nucleic acids are applicable, for example probes associated with fluorescence coloring materials, or radioactively-labeled probes.

According to an additional preferred embodiment of the third embodiment, the present invention concerns a process, in which the 5' end of the template tag sequence of the anchor oligonucleotide is identical to a part of the sequence of a detection nucleic acid, whereby the detection nucleic acid can be circular (target circle) or linear. The detection nucleic acid is added to the process and is optionally processed in the form that it is amplified in Step (c) of the method according to the invention. The processing initially includes a separation of the newly synthesized strand of nucleic acid from the template strand, whereby the strand separation is preferably carried out thermally, enzymatically and/or chemically. Amplification subsequently takes place. In a preferred embodiment, the detection nucleic acid is a target circle. The target circle refers to a closed nucleic acid ring, which can be composed of DNA or RNA, for example. This target circle can be amplified, for example with a polymerase by linear rolling circle amplification (RCA). The linear RCA of a target circle is sufficiently well known to the person skilled in the art. Thus, the 3' end of the newly synthesized strand of nucleic acid preferably binds to the target circle and there functions as a primer for the synthesis of a concatemer strand of nucleic acid complementary to the target circle. This requires a polymerase with strand displacement activity.

Furthermore, at least one other primer can be used in the embodiment described above, whereby at least the sequence of the 3' end of this primer is then identical with a subsequence of the target circle. Using at least one such primer enables an exponential amplification of the target circle (exponential RCA) with the newly synthesized strand of nucleic acid, which binds to the target circle with the 3' end of its tag sequence.

Finally, it is possible to attach at least one sequence to the resulting concatemer by means of the target circle, which enables the binding of at least one nucleic acid probe.

A fourth embodiment of the method according to the invention concerns the insertion of nucleic acids for fusing DNA fragments.

Preferably, in this fourth embodiment, RNA or DNA is used as template nucleic acid.

In the fourth embodiment of the method according to the invention, processing Step (d), is optionally carried out after Step (c), whereby, this step preferably includes initially a strand separation that can be carried out, for example, thermally, enzymatically and/or chemically. The resulting single strands can then be fused.

According to the fourth embodiment of the method according to the invention, the template tag sequence of the anchor oligonucleotide contains at least one functional sequence, which is so constructed that the complementary sequence inserted into the newly synthesized nucleic acid, that is the tag sequence, can self hybridize, that is, a newly synthesized strand of nucleic acid hybridizes with its 3' end with the 3' end of a second newly synthesized strand. In this case, two newly synthesized strands of nucleic acid are fused in that a polymerase is added, which in the presence of nucleotides fills up the single-stranded region to a double strand with nucleotides.

In a preferred embodiment of the fourth embodiment of the method according to the invention, Step (c) is carried out in the presence of a primer. This primer is a nucleic acid having either a specific, degenerate or random sequence in the region hybridized with the template nucleic acid. In the region of the 5' end, the primer preferably having a tag sequence, ideally a tag sequence that hybridizes with itself, i.e. hybridizes a newly synthesized strand of nucleic acid with its 5' end with the 5' end of a second newly synthesized strand. In this embodiment of the present invention, two or more newly synthesized strands of nucleic acid can hybridize together with their respective ends. Thus, linear or circular molecules can be formed.

In a further embodiment, single-stranded regions are filled up into double-stranded regions in an optional subsequent process step with a DNA polymerase and dNTPs in a buffer deemed appropriate by the person skilled in the art. Subsequent this processing step, the actual fusion takes place either enzymatically or chemically, i.e. by means known to or attained by the person skilled in the art. Fusion can take place, for example, with naturally-occurring ligases, or by chemical ligation, for example by thiophosphate (see U.S. Pat. No. 6,635,425), ligation by another ligating enzyme, for example topoisomerases or certain ribosomes. Thus, double-stranded circular or double-stranded linear DNA molecules are formed.

Optionally, the processing described above can contain an amplification reaction in an additional step, whereby the amplification can take place both isothermally (e.g. RCA with circular DNA molecules or MDA with linear DNA molecules), or non-isothermally (e.g., by PCR). Another optional step represents a sequencing of fused or fused and then amplified nucleic acids. Within the meaning of the present invention, sequencing refers to the detection of a sequence, as well as to the partial or complete determination of the nucleotide sequence.

A few exemplary embodiments are presented below to further illustrate the present invention.

Embodiment 1

This embodiment concerns RNA amplification according to the invention, from small starting amount. A schematic representation of this methodological variant is found in FIG. 2.

100 ng of total RNA are reverse transcribed with the Omniscript® RT Kit (QIAGEN GmbH, Hilden, Germany). The reverse transcriptase reaction (RT reaction) is carried out in the presence of nucleotides, 1 µM of oligo-dT primer and 10 µM of anchor oligonucleotide. The template tag sequence of the anchor oligonucleotide contains the sequence for an RNA polymerase promoter (here, T7 RNA polymerase promoter) in the 5' region and an 8-mer random sequence in the region of the 3' end. Subsequently, the cDNA is inserted in an in vitro transcription according to the MegaScript Kit® protocol (Ambion (Europe) Ltd., Huntington, UK). At this juncture, the small starting amount is strongly amplified to the total RNA in the sense direction.

In a modification of the experimental method described above, an anchor oligonucleotide, for example, can be also be used in such a manner that the anchor oligonucleotide, in addition to the insertion of a tag sequence, initiates the start of the DNA synthesis; therefore, the part hybridized with the template nucleic acid (anchor sequence) functions as a primer for the newly synthesized strand. In this case, the anchor oligonucleotide must contain a 3' end, such as, for example, a free 3'-OH end, that is extendable with a polymerase.

In a further modification of the experimental procedure described, an anchor oligonucleotide can contain, for example, a specific or degenerate sequence in the region of the anchor sequence, so that only a sequence or certain group of sequences can be amplified. In a further modification, random, degenerate or specific primers can be used instead of oligo-dT primers.

In a further modification of the experimental procedure described above, genomic DNA or other DNA can be used as a target nucleic acid in place of RNA. In this way, any sequence of genomes can be converted into RNA.

Embodiment 2

Figure 3:
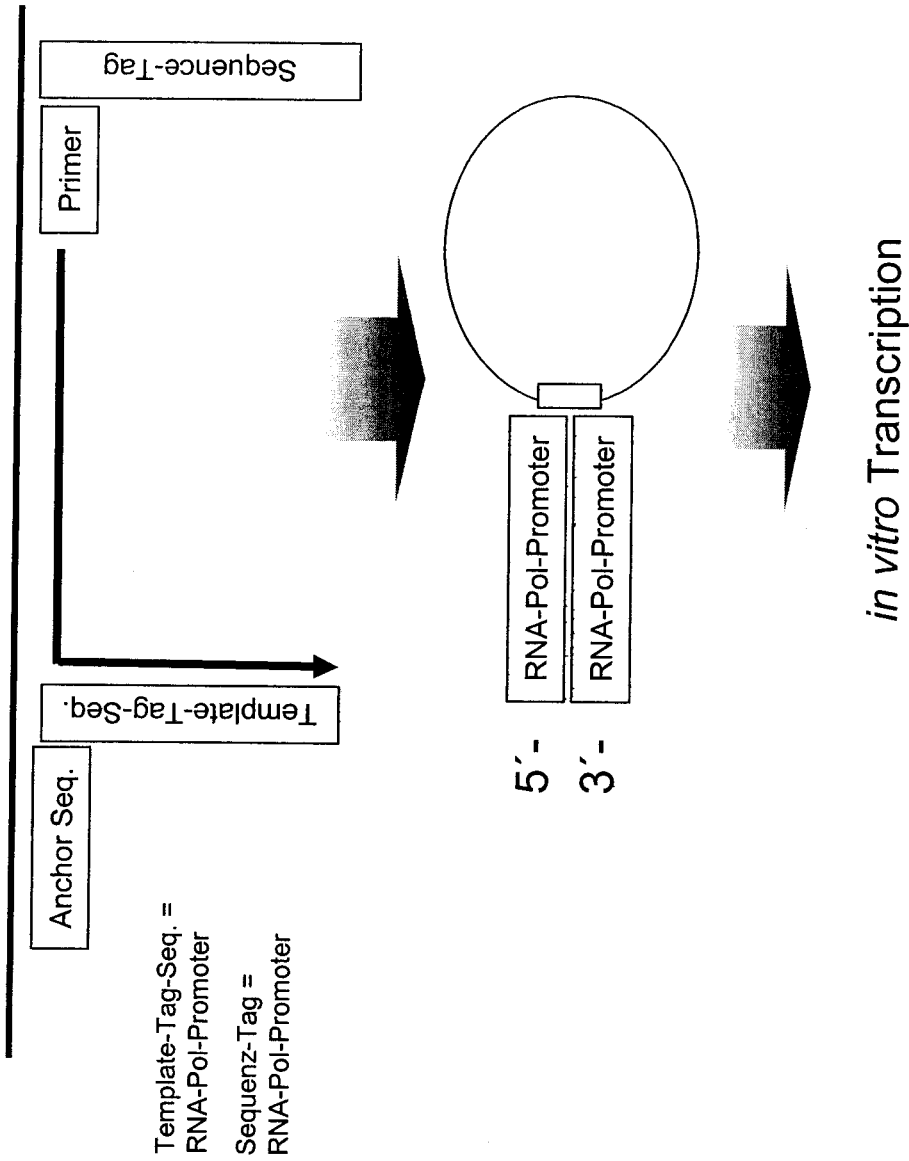
FIG. 3 shows a schematic representation of a further method according to the invention in the context of RNA amplification in which a promoter sequence is inserted during the synthesis of the new strand of nucleic acid, by doing so primer tag sequence containing the promoter sequence and the tag sequence of the newly synthesized strand inserted by the template tag sequence of the anchor oligonucleotide containing the promoter sequence hybridize on one another and thus form the promoter.

This embodiment also concerns an RNA amplification according to the invention. Unlike the RNA amplification according to Embodiment 1, a tag sequence is inserted at the 5' end of the newly synthesized nucleic acid by means of a primer with a tag sequence at its 5' end, in addition to the tag sequence at the 3' end of the newly synthesized nucleic acid, which was inserted by means of the template tag sequence of the anchor oligonucleotide. The primer tag sequence, as well as the template tag sequence of the anchor oligonucleotide both contains the promoter sequence. This leads to the tag sequences at the 3' end and 5' end of the newly synthesized nucleic acid being complementary to each other in the promoter range. After hybridization of the 3' end of the newly synthesized nucleic acid with the complementary 5' end of the newly synthesized strand of nucleic acid, the RNA polymerase can now bind to the double-stranded promoter and the in vitro transcription is initiated. A schematic representation of RNA amplification, in which the promoter sequence is inserted into the newly synthesized strand of nucleic acid by means of an anchor oligonucleotide during first-strand cDNA synthesis, is depicted in FIG. 3.

100 ng of total RNA are reverse transcribed with Omniscript®. The reverse transcriptase reaction (RT reaction) is carried out with RT buffers, nucleotides (0.5 mM) and anchor oligonucleotides (10 µM). The template tag sequence of the anchor oligonucleotide contains the sequence for the T7 RNA polymerase promoter in the 5' region and an 8-mer random sequence in the 3' region. In this reaction, the anchor oligonucleotide functions at the same time as a primer, i.e. the template tag sequence of the anchor oligonucleotide is considered to be a primer tag sequence in the case that the anchor oligonucleotide itself functions as a primer. After a RT reaction time of 60 minutes at 37° C., the reaction mixture is heated at 95° C. for 5 minutes. Afterwards, the cDNA is inserted in an in vitro transcription according to the MegaScript® Kit (Ambion) protocol. Here, the small starting amount is strongly amplified to the total RNA in the sense direction.

In a modification of the experimental procedure described above, an anchor oligonucleotide, for example, can also be used with alternative RNA polymerase promoters.

In a second modification of the experimental procedure described above, an anchor oligonucleotide can also have, for example, a specific or degenerate sequence in the region of the anchor sequence, so that only a transcript or certain group of transcripts can be amplified.

In a third modification of the experimental procedure described above, genomic DNA or other DNA can be inserted as a target nucleic acid in the place of RNA. Thus, any sequence of genomes, for example, can be converted into RNA.

Embodiment 3

Figure 4:
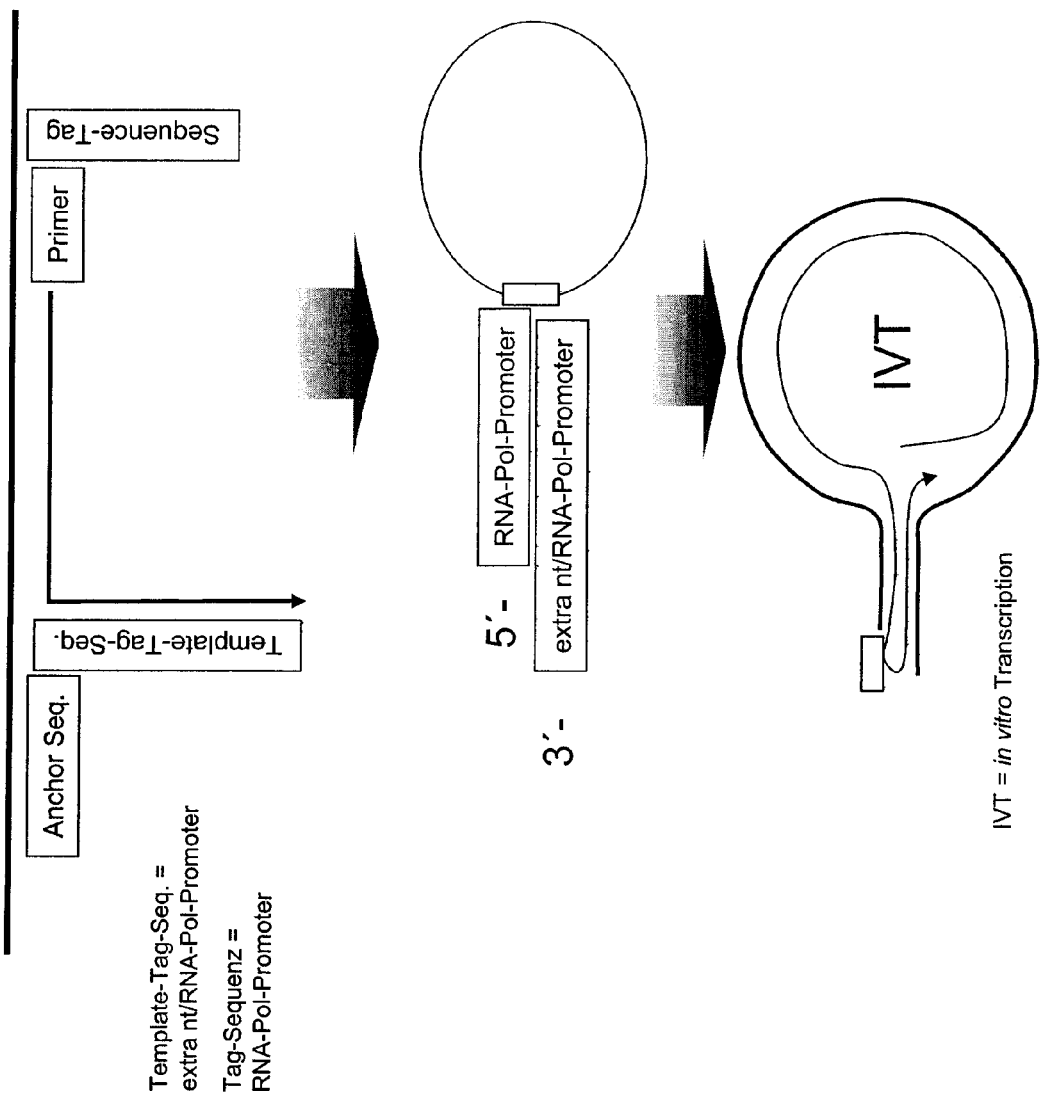
FIG. 4 shows a schematic representation of a further method according to the invention in the context of RNA amplification in which a promoter sequence is inserted during synthesis of the new strand of nucleic acid, by doing so primer tag sequence containing the promoter sequence and the tag sequence inserted by the template tag sequence of the anchor oligonucleotide containing the promoter sequence hybridize with each other and thus form the promoter, whereby the template tag sequence of the anchor oligonucleotide has at least one other nucleotide (extra nt) 5' of the promoter sequence.

Embodiment 3 concerns again an RNA amplification which represents a modification of the RNA amplification described in Embodiment 2. The difference is that the newly synthesized strand of DNA hybridizes to a hairpin structure with a 3' overhang. This is inserted into the newly synthesized nucleic acid by means of the template tag sequence of the anchor oligonucleotide. By using a 3' overhang, the RNA polymerase, in the transcription, stimulates the so-called template switch at the 5' recessive end, which results in an RNA molecule containing many copies of the same sequence in succession (concatemer). A schematized representation of RNA amplification is shown in FIG. 4, in which the promoter sequence is inserted by means of the template tag sequence of the anchor oligonucleotide during first-strand cDNA synthesis. Thus, the template tag sequence 5' of the promoter sequence has at least one additional base, which protrudes over the 5' end with the hybridization of the 3' end and 5' end of the newly synthesized nucleic acid.

100 ng of total RNA are reverse transcribed with Omniscript® (QIAGEN). The reverse transcriptase reaction (RT reaction) is carried out with RT buffers, nucleotides (0.5 mM), an anchor oligonucleotide (10 µM) and a primer. The primer tag sequence and the template tag sequence of the anchor oligonucleotide are identical; they contain the T7 RNA polymerase promoter. However, the template tag sequence of the anchor oligonucleotide has 3 additional nucleotides at the 3' end. After the RT reaction, lasting 60 minutes at 37° C., the reaction mixture is heated at 95° C. for 5 minutes. Afterwards, the cDNA is inserted in an in vitro transcription according to the MegaScript® Kit (Ambion) protocol. Here, the small starting amount is strongly amplified to the total RNA in the sense direction.

In a modification of the experimental procedure described above, an anchor nucleotide, for example, can be used with alternative RNA polymerase promoters.

According to a second modification of the experimental procedure described above, an anchor oligonucleotide can have, for example, a specific or degenerate sequence in the region of the anchor sequence, so that only a transcript or certain group of transcripts can be amplified.

In a third modification of the experimental procedure described above, genomic DNA or other DNA can also be used as a target nucleic acid in the place of RNA. Thus, any sequence of genomes, for example, can be converted into RNA.

Embodiment 4

This embodiment concerns an anchor oligonucleotide for signal amplification by so-called rolling circle amplification (RCA). An aim of this procedure is to amplify a signal starting from a certain sequence or group of sequences by in vitro DNA synthesis with DNA or RNA as a template nucleic acid. In the method according to the invention, an anchor oligonucleotide is required that has an anchor sequence which can hybridize to the template nucleic acid, whereby the template tag sequence of the anchor oligonucleotide is identical to a sequence section of a circular nucleic acid molecule (target circle), so that the tag sequence inserted into the newly synthesized strand by means of the template tag sequence of the anchor oligonucleotide hybridizes with its 3' end with the target circle and functions as a primer in a subsequent RCA (schematic representation in FIG. 5).

Figure 5:
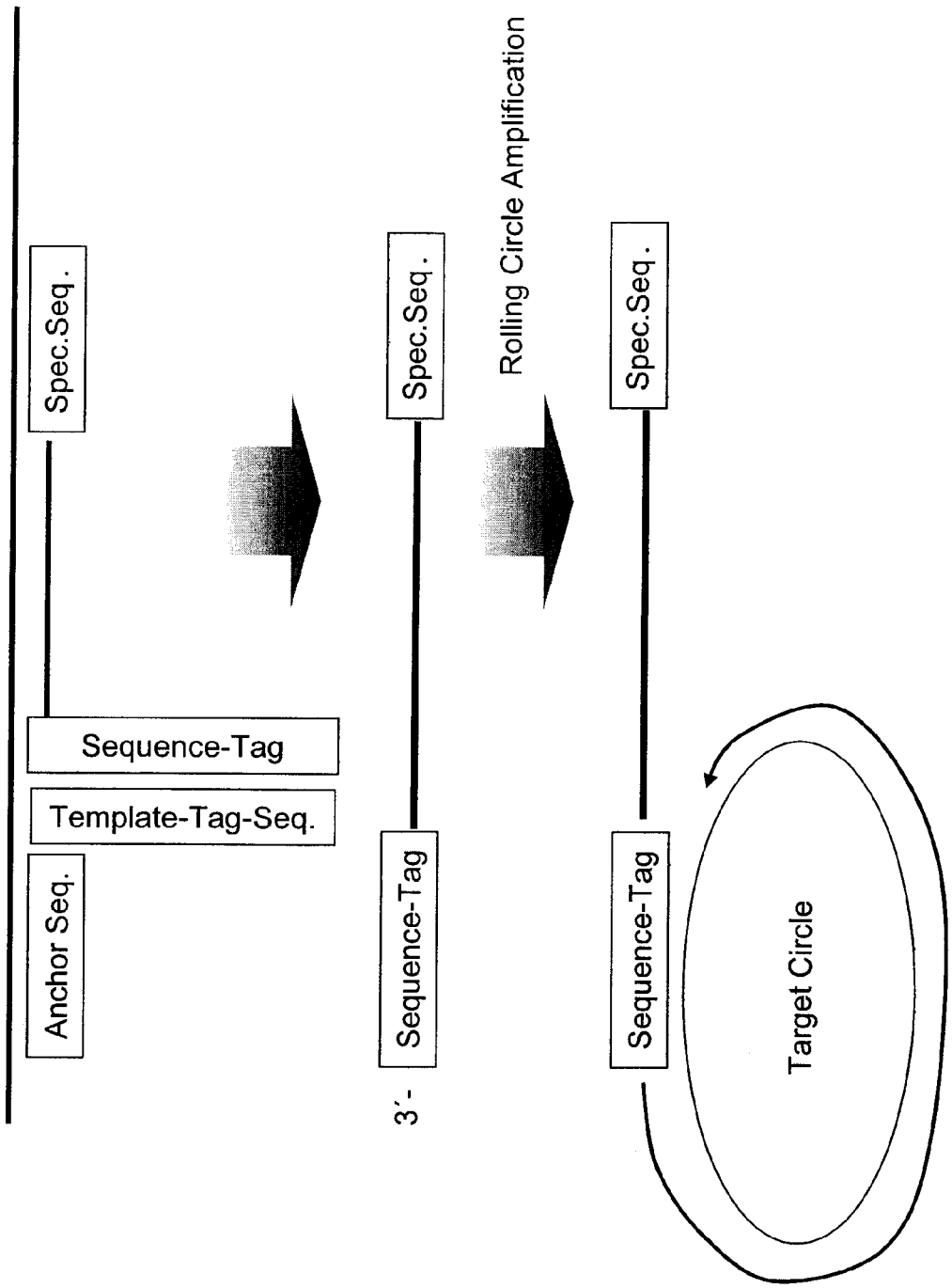
FIG. 5 shows a schematic representation of a generically applicable method according to the invention in the context of signal amplification, in which, during the synthesis of the new strand of nucleic acid by means of the template tag sequence of the anchor oligonucleotide, a tag sequence is inserted into the newly synthesized strand, whereby the newly synthesized strand can bind a target circle to its 3' end by means of its tag sequence and thus can function as a primer in subsequent signal amplification by rolling circle amplification.

100 ng of total RNA in an RT reaction are rewritten into cDNA with Omniscript® (QIAGEN), RT buffer, dNTPs, 1 µM of actin primer (designated in FIG. 5 by "Spec.Seq") and a β-actin anchor oligonucleotide (the β-actin anchor oligonucleotide is designated by "anchor" in FIG. 5), according to the Omniscript® protocol. The β-actin anchor oligonucleotide has, on the one hand, an anchor sequence binding β-actin transcript, and on the other a template tag sequence originating from single-stranded DNA phage M13. The sequence of the β-actin primer binds 3' in relation to the binding site of the β-actin anchor oligonucleotide in the transcript. In cDNA synthesis, the tag sequence which serves as a primer in the rolling circle amplification of the DNA phage Ml3 is inserted. The cDNA is purified by the QIAquick® (QIAGEN) standard protocol. The rolling circle amplification is carried out in a 50 µl reaction batch containing phi29 DNA polymerase, buffer, nucleotides and M13 DNA. The starting amount is strongly amplified to the M13 DNA.

In a modification of the experimental procedure described above, for example, an anchor oligonucleotide can be used in such a way that the tag sequence at the 3' end of the newly synthesized nucleic acid binds alternative target circles and functions as a primer with them.

In a second modification of the experimental procedure described above, anchor oligonucleotides with random, degenerate or other specific sequences can be used as anchor sequences and/or the synthesis of the new strand of nucleic acid can be activated by random, degenerate, other specific or oligo-dT primers.

According to a third modification of the experimental procedure described above, genomic DNA or other DNA can be inserted as a template nucleic acid in place of the RNA.

Embodiment 5

Figure 8:
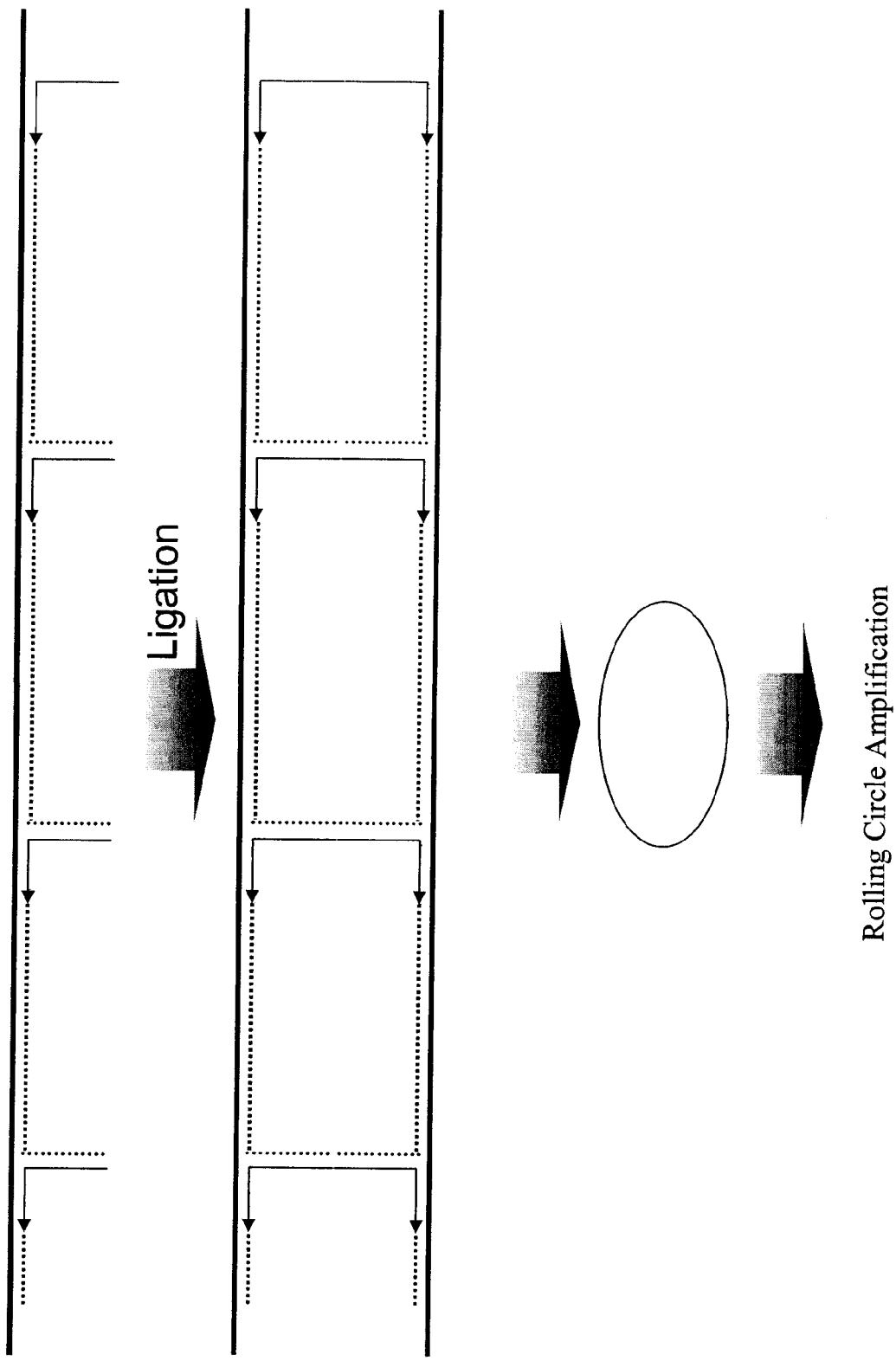
FIG. 8 shows a schematic representation of an additional generically applicable method according to the invention in the context of DNA amplification, in which during the synthesis of the new strand of nucleic acid starting from RNA or DNA a tag sequence is inserted at the 3' end of the newly synthesized nucleic acid by means of the template tag sequence of the anchor oligonucleotide. Furthermore, a primer having a tag sequence that can be different from or the same as the template tag sequence of the anchor oligonucleotide is used. The resulting double-stranded ends are ligated; subsequently the newly synthesized strands of nucleic acid are separated from the template strands and form circular single-stranded nucleic acids, which can then be amplified by rolling circle amplification.

This further embodiment concerns DNA amplification. This embodiment of the present invention corresponds to the steps depicted in Example 1 (see below). Here again, a tag sequence was inserted at the 5' end of the newly synthesized nucleic acid with a primer with a tag sequence at its 5' end, in addition to the tag sequence being inserted at the 3' end of the newly synthesized nucleic acid by means of the template tag sequence of the anchor oligonucleotide. However, in the present embodiment, no separation of the newly synthesized strand of nucleic acid from the template nucleic acid is carried out before the ligation reaction, in contrast to Example 1. The ligation products, as in Example 1, consist of two sequences, which are fused to the tag sequences. These can be amplified by RCA after strand separation (schematic representation in FIG. 8).

100 ng of a gDNA are denatured. A polymerase reaction is carried out on the single strands, here with Omniscript® (QIAGEN). The polymerase reaction is carried out in the presence of a suitable buffer, nucleotides (0.5 mM), primers and anchor oligonucleotides (10 µM). The template tag sequence of the anchor oligonucleotide contains a specific sequence (here, a T7 promoter) in the 5' region and an 8-mer random sequence in the 3' region. In this embodiment, the primer used and the anchor oligonucleotide have an identical sequence. After reaction time of 60 minutes at 37° C., the DNA is ligated with T4 ligase. The resulting ligation products are heated at 95° C. and then are amplified with the REPLI-g® Kit (QIAGEN) in an RCA reaction. Thus, the starting amount is strongly amplified to the gDNA.

In a modification of the experimental procedure described above, an anchor oligonucleotide can be used, for example, with alternative template tag sequences.

In a second modification of the experimental procedure described, an anchor oligonucleotide can have, for example, a specific or degenerate sequence in the region of the anchor sequence, so that only one sequence or certain group of sequences can be amplified. Also, the anchor sequence can have an alternate length.

Example 1, described below, can also contain further embodiments. In a modification to the experimental procedure described in Example 1, for example an anchor oligonucleotide with alternative template tag sequences can be used.

In a further modification of the experimental procedure described in Example 1, an anchor oligonucleotide can have, for example, a specific or degenerate sequence in the region of the anchor sequence, so that only one sequence or certain group of sequences can be amplified. Also, the anchor sequence can have an alternate length.

In a third modification of the experimental procedure described in Example 1, a DNA polymerase can be present during the ligase reaction. This can contain exonuclease activity in addition to DNA polymerase activity. Should in the case of a large length of the newly synthesized nucleic acid, for example, no blunt ends form in the intramolecular hybridization, but instead sticky ends, the resulting gaps can be filled by the polymerase.

In a fourth modification of the experimental procedure described in Example 1, an oligonucleotide can be present during the ligase reaction, that forms a blunt-end hairpin structure by intramolecular hybridization and is subsequently ligated with the blunt end of the newly synthesized nucleic acid hybridized to the hairpin structure to the closed circular nucleic acid molecule.

Embodiment 6

This embodiment concerns the DNA amplification of methylated DNA sections. This form of amplification starts according to Example 1 (see below). In the present embodiment, a tag sequence was inserted at the 5' end of the newly synthesized nucleic acid with a primer with a tag sequence at its 5' end, in addition to the tag sequence being inserted at the 3' end of the newly synthesized nucleic acid by means of the template tag sequence of the anchor oligonucleotide. The primer tag sequence and the template tag sequence of the anchor oligonucleotide contain an identical sequence. This leads to the tag sequences at the 3' end and 5' end of the newly synthesized nucleic acid being complementary to each other. Following the synthesis of the new strand of nucleic acid, which is complementary to the partially methylated DNA, it is cut with methylation-sensitive restriction endonucleases. Subsequently, strand separation is carried out by incubation at 95° C. for 5 minutes.

Figure 9:
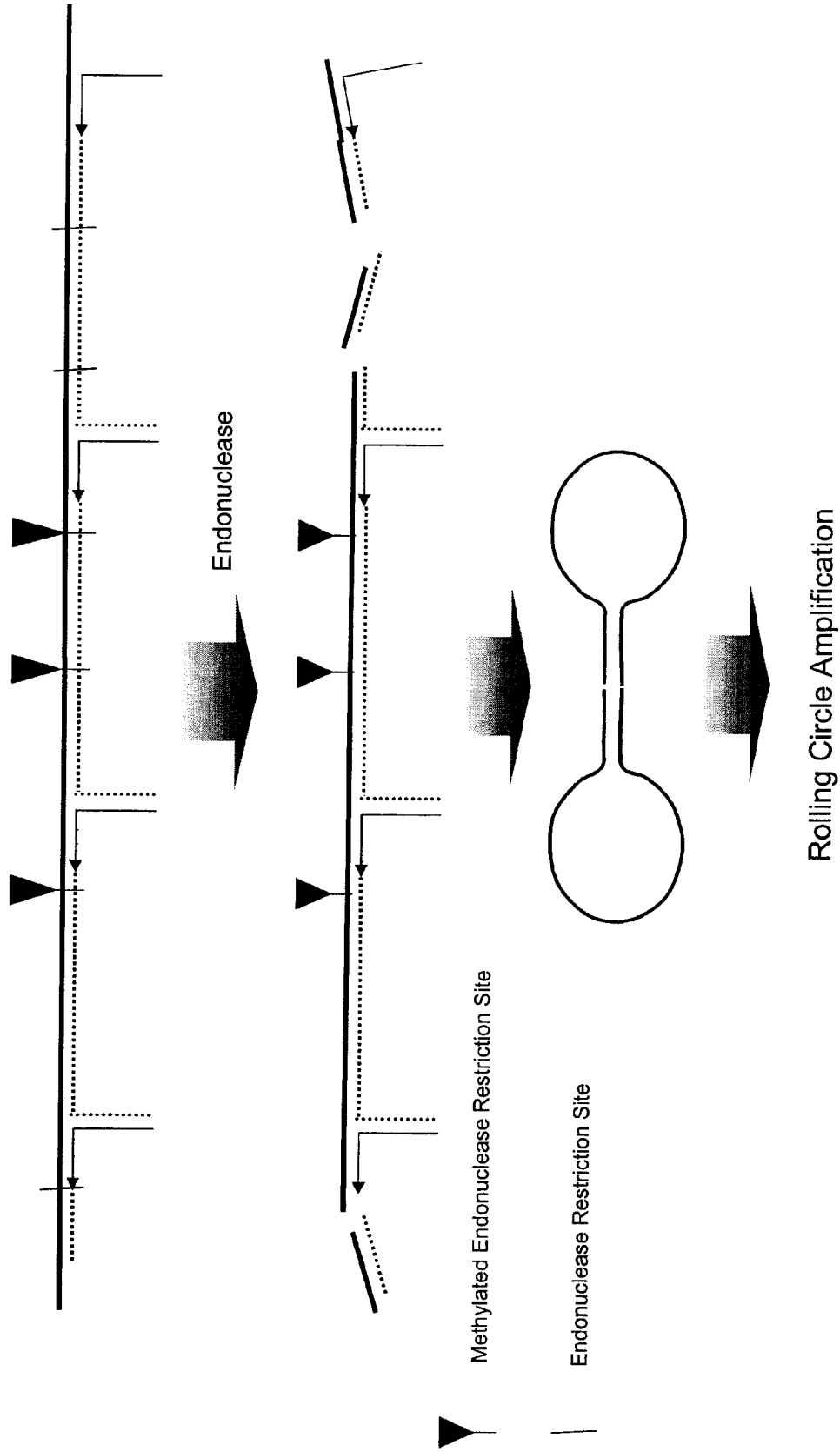
FIG. 9 shows a schematic representation of a generically applicable method according to the invention in the context of selective amplification of methylated DNA sections (methylated bases are shown by a triangle). A tag sequence, complementary to the primer tag sequence, is inserted at the 3' end of the newly synthesized nucleic acid by means of the template tag sequence of the anchor oligonucleotide during a nucleic acid synthesis reaction starting from DNA. After the nucleic acid synthesis reaction, the DNA is cut by methylation-sensitive restriction endonucleases. Afterwards, the newly synthesized strand of nucleic acid is separated from the template strand. Intramolecular hairpin structures can now form in the sections of DNA not cut, i.e. the methylated regions. These can be used for ligation reactions in order to amplify the nucleic acids in a subsequent rolling circle amplification reaction.

After hybridization of the 3' end of the newly synthesized nucleic acid with the complementary 5' end of the newly synthesized strand, a hairpin structure containing blunt, double-stranded ends forms with the uncut newly synthesized strand. Two such hairpin loops are ligated in "blunt-end" ligation, so that a dumbbell-shaped, circular DNA molecule is formed. In this way, methylated DNA can be amplified by RCA, while non-methylated DNA cannot be amplified (schematic representation in FIG. 9).

In a fourth modification of the experimental procedure, an oligonucleotide can be present during the ligase reaction so that a blunt end hairpin structure is formed by intramolecular hybridization and subsequently ligated with the blunt end of the newly synthesized nucleic acid hybridized to the hairpin structure to the closed circular nucleic acid molecule.

100 ng of dDNA were denatured. A polymerase reaction is carried out on the single strands, here with Omniscript® (QIAGEN). The polymerase reaction is carried out in the presence of a suitable buffer, nucleotides (0.5 mM), primers and anchor oligonucleotides (10 µM). The template tag sequence of the anchor oligonucleotide contains a specific sequence (here, a T7 promoter) in the 5' region and an 8-mer random sequence in the 3' region. The primers have a sequence identical to the anchor oligonucleotides. After an hour at 37° C., the DNA is treated with a methylation-sensitive restriction endonuclease, HpaII in the present embodiment, so that only non-methylated regions can be digested but methylated regions remain intact. The DNA is subsequently heated for five minutes at 95° C., thus denatured, and then ligated with T4 ligase. The resulting ligation products are amplified with the REPLI-g® Kit (QIAGEN) in an RCA reaction. Thus, the starting amount is strongly amplified to the methylated DNA.

In variation to the use of the HpaII restriction enzyme described, other enzymes can also be used, for example AatII, BcnI, Bsh1236I, Bsh1285I, BshTI, Bsp68I, Bsp119I, Bsp143II, Bsu15I, CseI, Cfr10I, Cfr42I, CpoI, Eco47III, Eco52I, Eco72I, Eco88I, Eco105I, EheI, Esp3I, FspAI, HhaI, Hin1I, Hin6I, HpaII, Kpn2I, MbiI, MluI, NotI, NsbI, PauI, PdiI, Pfl23II, Psp1406I, PvuI, SalI, SgsI, SmaI, SmuI, SsiI, TaiI, TauI, XhoI, etc.

According to a further modification of the experimental procedure described, the DNA is digested not by a methylation-sensitive restriction endonuclease, but instead by an isochizomer that digests both methylated and non-methylated DNA (e.g. the isoschizomer of HpaII is Msp1). Amplification of the ligation products leads to amplification of the residual DNA.

Embodiment 7

This embodiment concerns the use of anchor oligonucleotides according to the invention, for DNA cloning, in which the restriction endonuclease restriction site is inserted during the synthesis of the newly synthesized strand of nucleic acid by means of the template tag sequence of the anchor oligonucleotide. Denaturing of the newly synthesized strand of nucleic acid and template strand is subsequently carried out by second-strand synthesis, which results in a double strand sequence recognizable by a restriction endonuclease.

DNA or RNA can be used as template nucleic acids. Thus, DNA synthesis is carried out starting from the first primer, according to the template switch, up to the 5' end of the anchor oligonucleotide, whereby a tag sequence is inserted at the 3' end of the newly synthesized nucleic acid by means of the anchor oligonucleotide. In some embodiments, a restriction site is required in the sequence of the first primer. In addition, the anchor oligonucleotide contains one or more restriction sites in its sequence in this embodiment, whereby a ligation is possible after restriction digestion. For example, a ligation can result with cut vector DNA, e.g. for cloning purposes.

Figure 10:
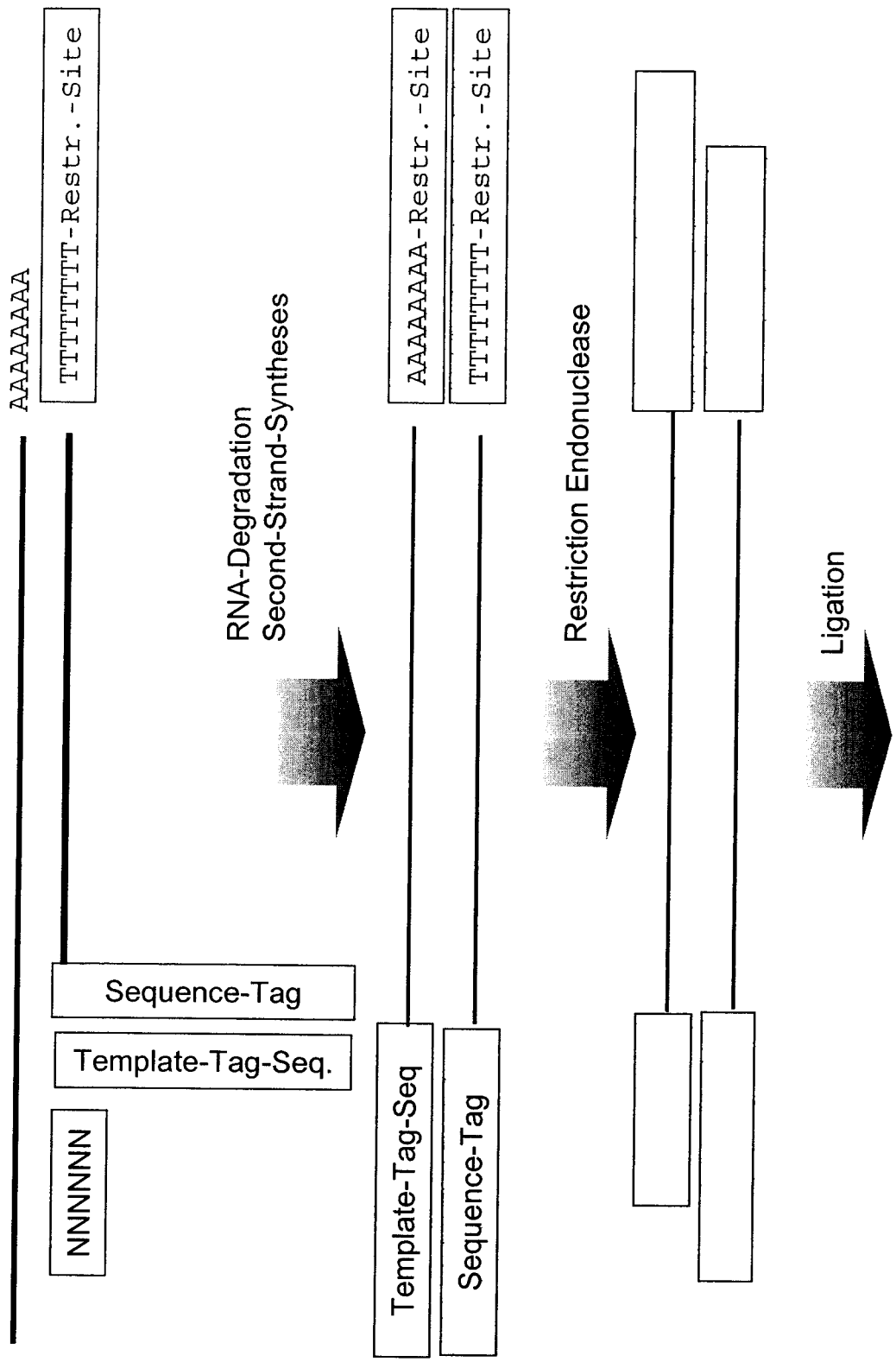
FIG. 10 shows a schematic representation of a method according to the invention in the context of DNA cloning, in which the restriction endonuclease restriction site is inserted by means of the template tag sequence of the anchor oligonucleotide during the synthesis of the new strand of nucleic acid. Denaturing of the newly synthesized strand of nucleic acid and template strand follows; next, second-strand synthesis is carried out, through which a double-strand sequence recognizable with a restriction endonuclease is formed.

1µ of total RNA in an RT reaction is rewritten into cDNA with a reverse transcriptase, RT buffer, dNTPs, 1 µM of oligo-dT primer, (containing the sequence of a Not1 restriction site at the 5' end) and 10 µM of an anchor oligonucleotide (containing the sequence of a Not1 restriction site at the 5' end), according to the standard Omniscript® protocol. On the one hand, the anchor oligonucleotide has a random sequence as hybridizing as an anchor. In cDNA synthesis, a tag sequence is inserted by means of the anchor oligonucleotide at the 3' end of the newly synthesized strand of nucleic acid, which contains the Not1 restriction site. Next, the second strand of the cDNA is produced in a standard reaction with the Klenow fragment, dNTPs and a primer whose sequence is identical to a part of the template tag sequence of the attached anchor oligonucleotide. The cDNA is purified following the QIAquick® (QIAGEN) standard protocol and subsequently cut with Not1, after which the ligation with a vector cut with Not1 is carried out (schematic representation in FIG. 10). The vector is then transformed into competent *E. coli* cells. The overnight culture is purified by known methods and lysed and the plasmid is isolated. In this way, the starting amount of the cDNA obtained from the inserted RNA is amplified.

In a modification of the experimental procedure described above, an anchor oligonucleotide can be used, for example, with a specific or degenerate anchor sequence.

According to a further modification of the experimental procedure described above, the cDNA synthesis can be started via either random or specific primers bearing a restriction site for a restriction enzyme on their 5' end.

Embodiment 8

This embodiment concerns the use of anchor oligonucleotides according to the invention for DNA amplification in which the restriction endonuclease restriction site is inserted via the template tag sequence of the anchor oligonucleotide during the synthesis of the newly synthesized strand of nucleic acid. Denaturing of the newly synthesized strand of nucleic acid and template strand follows, and second strand synthesis is then carried out when a double-strand sequence recognizable with a restriction endonuclease is formed.

DNA or RNA can be used as template nucleic acids. Thus, DNA synthesis can then be carried out starting from a first primer, according to the template switch, up to the 5' end of the anchor oligonucleotide, whereby a tag sequence is inserted at the 3' end of the newly synthesized nucleic acid by means of the anchor oligonucleotide. In some embodiments, a restriction site is required in the sequence of this first primer. In addition, in this embodiment the anchor oligonucleotide contains one or more restriction sites in its sequence, whereby an intramolecular ligation of the newly synthesized strand of nucleic acid is possible after restriction digestion.

Figure 11:
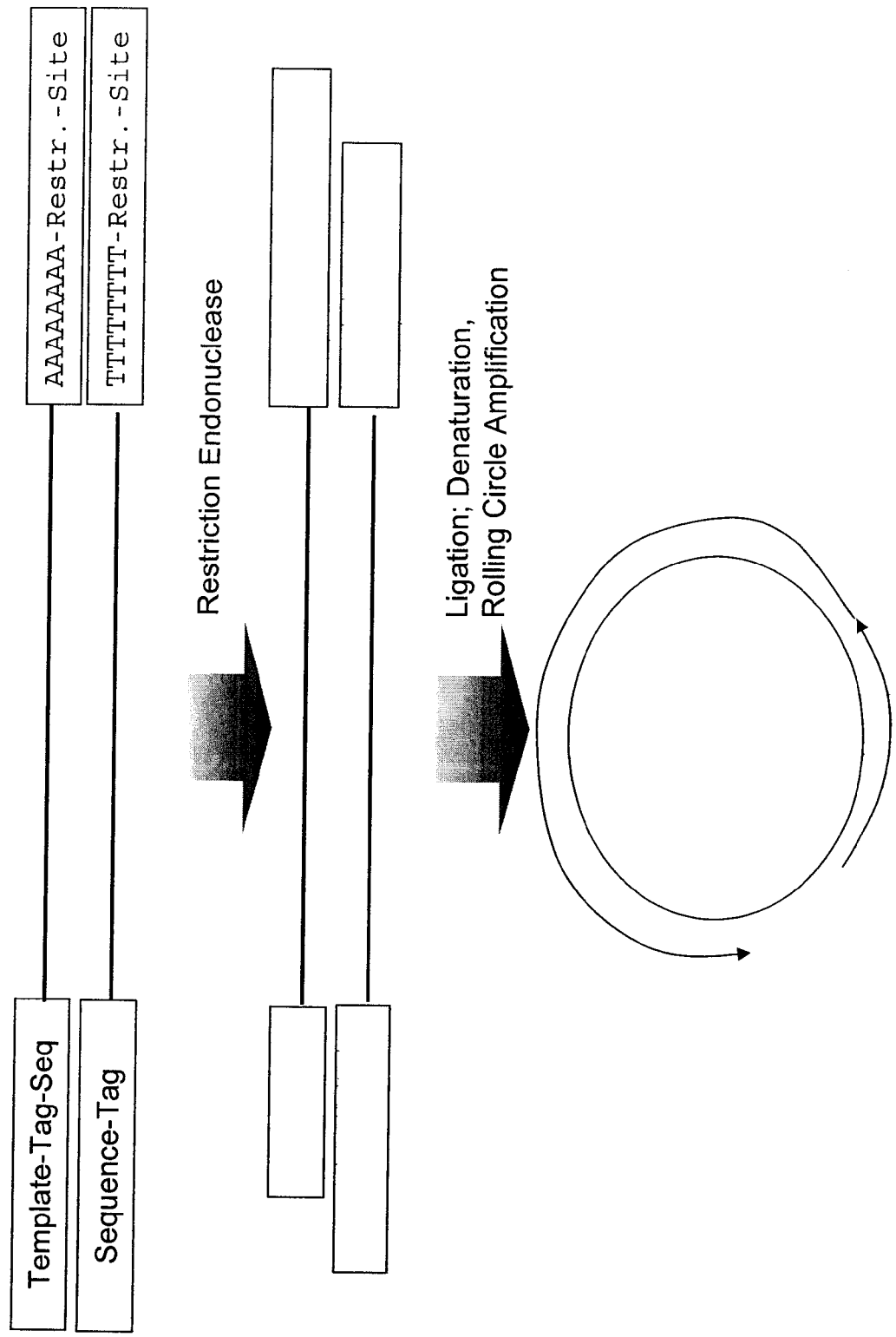
FIG. 11 shows a schematic representation of a method according to the invention in the context of DNA amplification, in which the restriction endonuclease restriction site is inserted by means of the template tag sequence of the anchor oligonucleotide during the synthesis of the new strand of nucleic acid. Likewise, the primer contains a restriction endonuclease restriction site. Compatible restriction sites are inserted via the anchor oligonucleotide and primer. Denaturing of the newly synthesized strand of nucleic acid and template strand follows; next, second-strand synthesis is carried out, through which a double-strand sequence recognizable with a restriction endonuclease is formed. After the restriction digestion of both ends, subsequent intramolecular hybridization and eventual ligation, double-stranded circular nucleic acids are formed, which can then be amplified by rolling circle amplification.

For example, the tag sequence can function as a primer binding site for rolling circle amplification. Thus, the whole transcriptome, or also genome, can be amplified (FIG. 11).

0.1μ of total RNA in an RT reaction is rewritten into cDNA with a reverse transcriptase, RT buffer, dATP, dCTP, dGTP, dTTP, 1 μM of oligo-dT primer (containing the sequence of a Not1 restriction site at the 5' end) and 10 μM of an anchor oligonucleotide according to the standard Omniscript® protocol (QIAGEN). On the one hand, the anchor oligonucleotide has a random sequence as a hybridizing anchor, and, on the other hand, a template tag sequence, which likewise contains a Not1 restriction site. In cDNA synthesis, a tag sequence is inserted by means of the anchor oligonucleotide at the 3' end of the newly synthesized nucleic acid, which contains the Not1 restriction site. Next, the second strand of the cDNA is produced in a standard reaction with the Klenow fragment, dNTPs and a primer, whose sequence is identical to a portion of the template tag sequence of the attached anchor oligonucleotide. The cDNA is purified by the QIAquick® (QIAGEN) standard protocol and subsequently cut with Not1. This DNA is then ligated in a 1000 μl ligation reaction with T4 ligase when predominantly circular DNA molecules are formed. The resulting circular DNA molecules are increased by RCA (a schematic representation is found in FIG. 11).

In a modification of the experimental procedure described, an anchor oligonucleotide can be used, for example with a specific or degenerate anchor sequence. In a further modification, the cDNA synthesis can be started with random or specific primers containing a restriction site for a restriction enzyme on their 5' ends.

Embodiment 9

Figure 12:
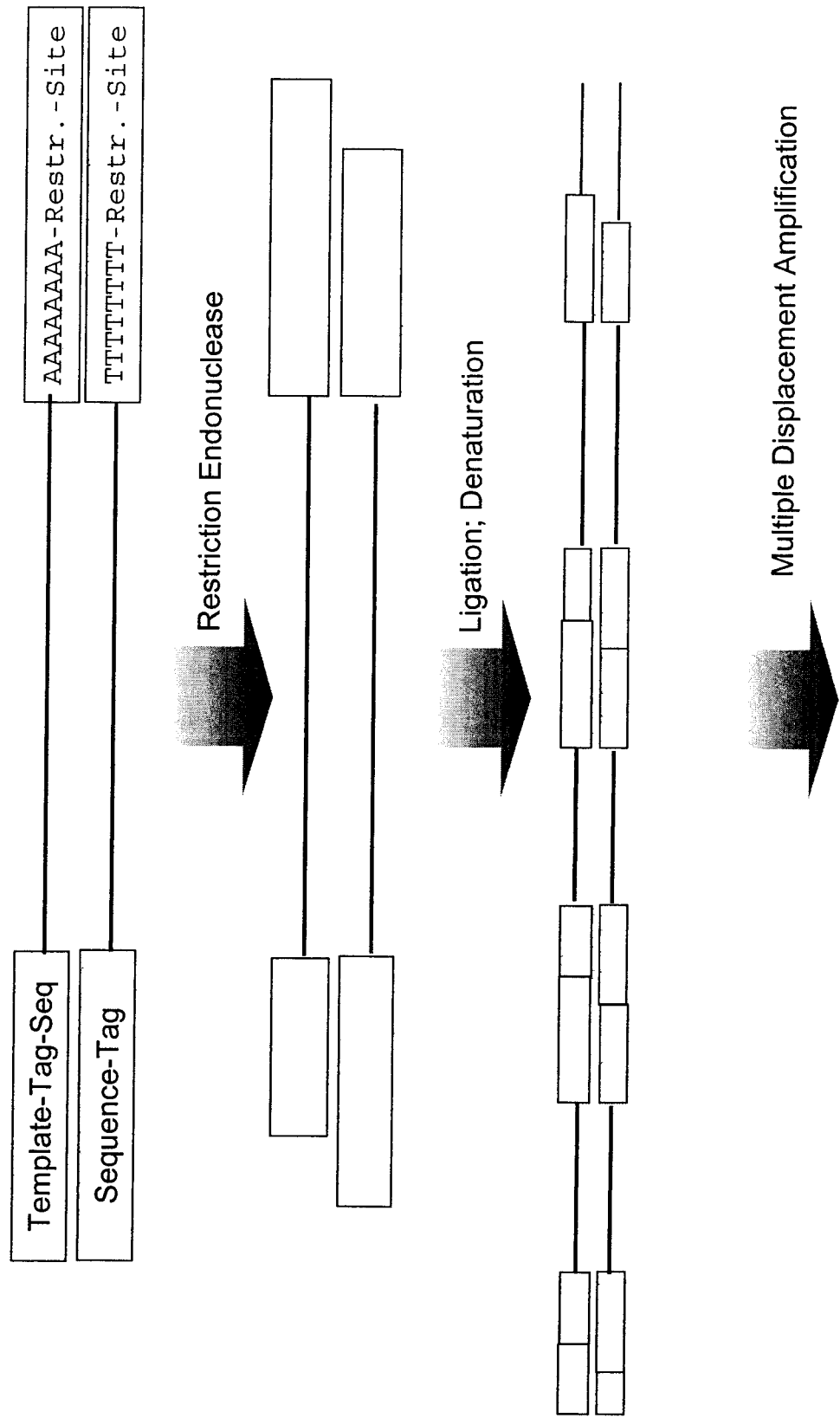
FIG. 12 shows a schematic representation of a method according to the invention in the context of DNA amplification, in which the restriction endonuclease restriction site is inserted by means of the template tag sequence of the anchor oligonucleotide during the synthesis of the new strand of nucleic acid. Likewise, the primer contains a restriction endonuclease restriction site. Compatible restriction sites are inserted via the anchor oligonucleotide and primer. Denaturing of the newly synthesized strand of nucleic acid and template strand follows; next, second-strand synthesis is carried out, through which a double-strand sequence recognisable with a restriction endonuclease is formed. After the restriction digestion of both ends, subsequent intramolecular hybridization and eventual ligation, double-stranded linear nucleic acids are formed, which can then be amplified by multiple displacement amplification (MDA).

This embodiment too concerns the use of anchor nucleotides for inserting a restriction site for restriction endonucleases into a nucleic acid for producing large molecules. Whereas Embodiment 8, however, concerns circular DNA molecules, Embodiment 9 concerns the production of linear DNA molecules. DNA or RNA can be used as target nucleic acids. Thus, DNA synthesis can be carried out starting from the first primer, according to the template switch, up to the 5' end of the anchor oligonucleotide, whereby a tag sequence is inserted at the 3' end of the newly synthesized nucleic acid by means of the anchor oligonucleotide. In some embodiments, a restriction site in the sequence of this first primer is required. In addition, in this embodiment the anchor oligonucleotide contains one or more restriction sites in its sequence, whereby an intramolecular ligation of the newly synthesized strand of nucleic acid can be realized after restriction digestion (a schematic representation is found in FIG. 12).

0.1μ of total RNA in an RT reaction is rewritten into cDNA with a reverse transcriptase, RT buffer, dATP, dCTP, dGTP, dTTP, 1 μM of oligo-dT primer (containing the sequence of a Not1 restriction site at the 5' end) and 10 μM of an anchor oligonucleotide according to the standard Omniscript® protocol (QIAGEN). On the one hand, the anchor oligonucleotide has a random sequence as hybridizing anchor sequence, and, on the other hand, a template tag sequence, which likewise contains a Not1 restriction site. In cDNA synthesis, a tag sequence is inserted by means of the anchor oligonucleotide to the 3' end of the newly synthesized nucleic acid, which contains the Not1 restriction site. The second strand of the cDNA is produced next in a standard reaction with Omniscript®, dNTPs and a primer whose sequence is identical to a portion of the template tag sequence of the inserted anchor oligonucleotide. The cDNA is purified according to the QIAquick® (QIAGEN) standard protocol and subsequently cut with Not1. The reaction mixture is heated for five minutes at 65° C., thus inactivating Not1. An aliquot is then ligated to concatemers in a 20 μl ligation reaction with T4 ligase. The ligation products are amplified in MDA according to the standard Repli-g® protocol for cleaned DNA (QIAGEN).

In a modification of the experimental procedure described, an anchor oligonucleotide can be used, for example, with a specific or degenerate anchor sequence. In a further modification, the cDNA synthesis can be started via random or specific primers.

Embodiment 10

Figure 13:
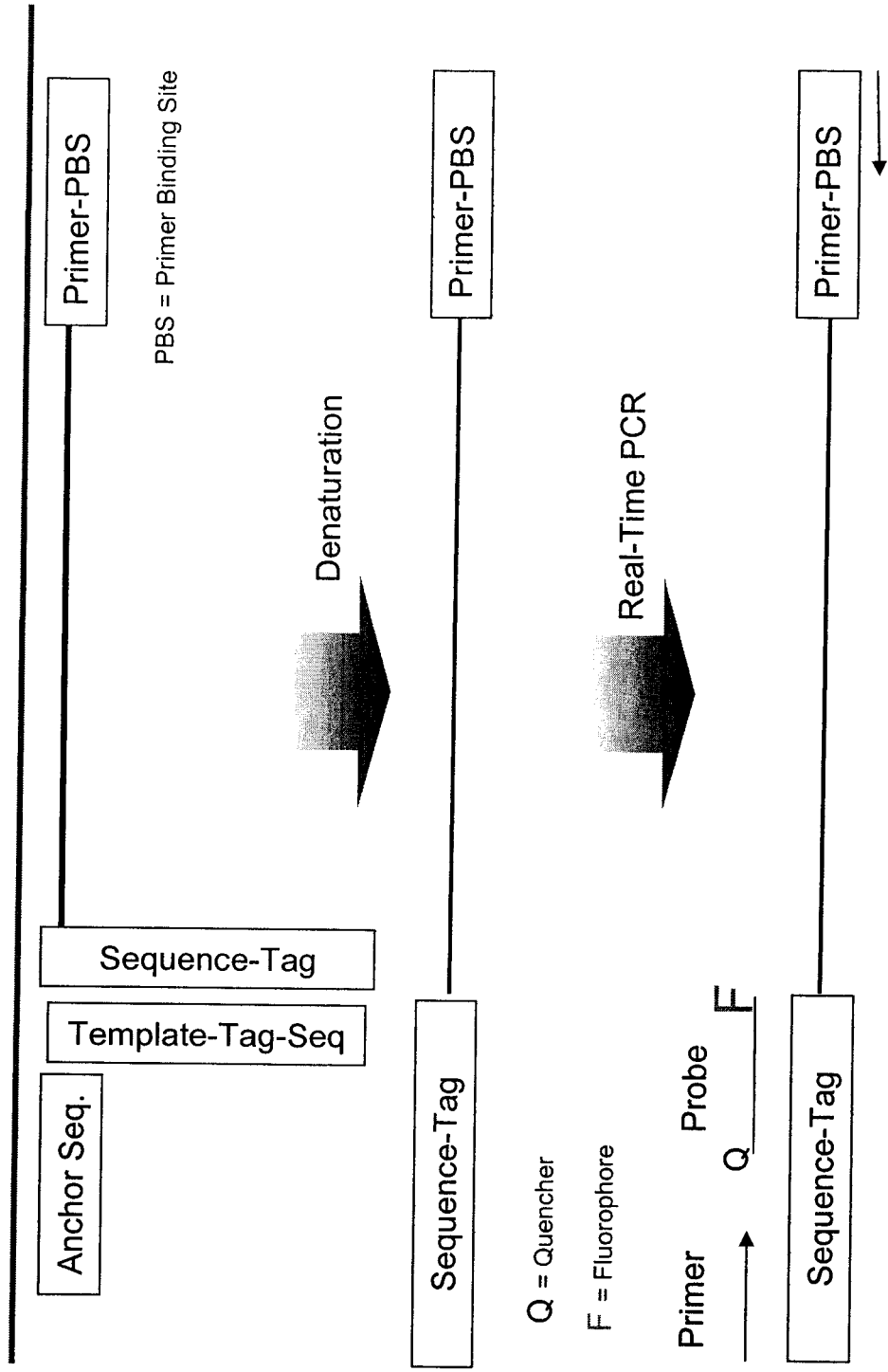
FIG. 13 shows a schematic representation of a method according to the invention in the context of a nucleic acid detection reaction by real-time PCR, in which a probe/primer binding site is inserted by means of the template tag sequence of the anchor oligonucleotide during the synthesis of the new strand of nucleic acid.

This embodiment concerns the insertion of anchor oligonucleotides for detecting DNA in a real-time PCR. In this embodiment of the method according to the invention, a primer binding site is inserted into the newly synthesized nucleic acid by means of the anchor oligonucleotide. The tag sequence inserted into the newly synthesized nucleic acid additionally functions as a probe binding site for the primer binding site 3' from this, so that the synthesized molecules of nucleic acid can be quantified in a real-time PCR. DNA or RNA can be used as target nucleic acids. In the case of RNA, DNA synthesis is carried out, for example, starting from a first oligo-dT primer having a tag containing a primer binding site, according to the template switch, up to the 5' ends of the anchor oligonucleotide, whereby a tag sequence is inserted at the 3' end of the newly synthesized nucleic acid by means of the anchor oligonucleotide. The real-time PCR can be quantified using a SYBR Green RT-PCR Kit (QIAGEN). In a modification of the method, a probe-based, real-time PCR can also be carried out. The prepared reaction for the real-time PCR analysis of cDNA is schematically represented in FIG. 13, in which probe and primer binding sites are inserted into the newly synthesized strand during the new nucleic acid strand synthesis.

0.01 µg of total RNA was rewritten into cDNA in an RT reaction with reverse transcriptase, RT buffer, dNTP, 1 µM of oligo-dT primer (with a primer binding site) and 1 µM of an anchor oligonucleotide according to standard RT protocol. The anchor oligonucleotide contains a random sequence as a hybridizing anchor and a template tag sequence, whereby a primer and probe binding site is inserted at the 3' end of the newly synthesized nucleic acid. A real-time PCR is now carried out in a real-time PCR with QuantiTect® reagents (QIAGEN) and the primers, which hybridize to the attached primer binding sites. The nucleic acid can be quantified during amplification by comparison with a nucleic acid standard.

In a further modification of the experimental procedure described, an anchor oligonucleotide can be used, for example, with a specific or degenerate sequence. In a further modification, cDNA synthesis can be initiated by random or specific primers.

Embodiment 11

Figure 14:
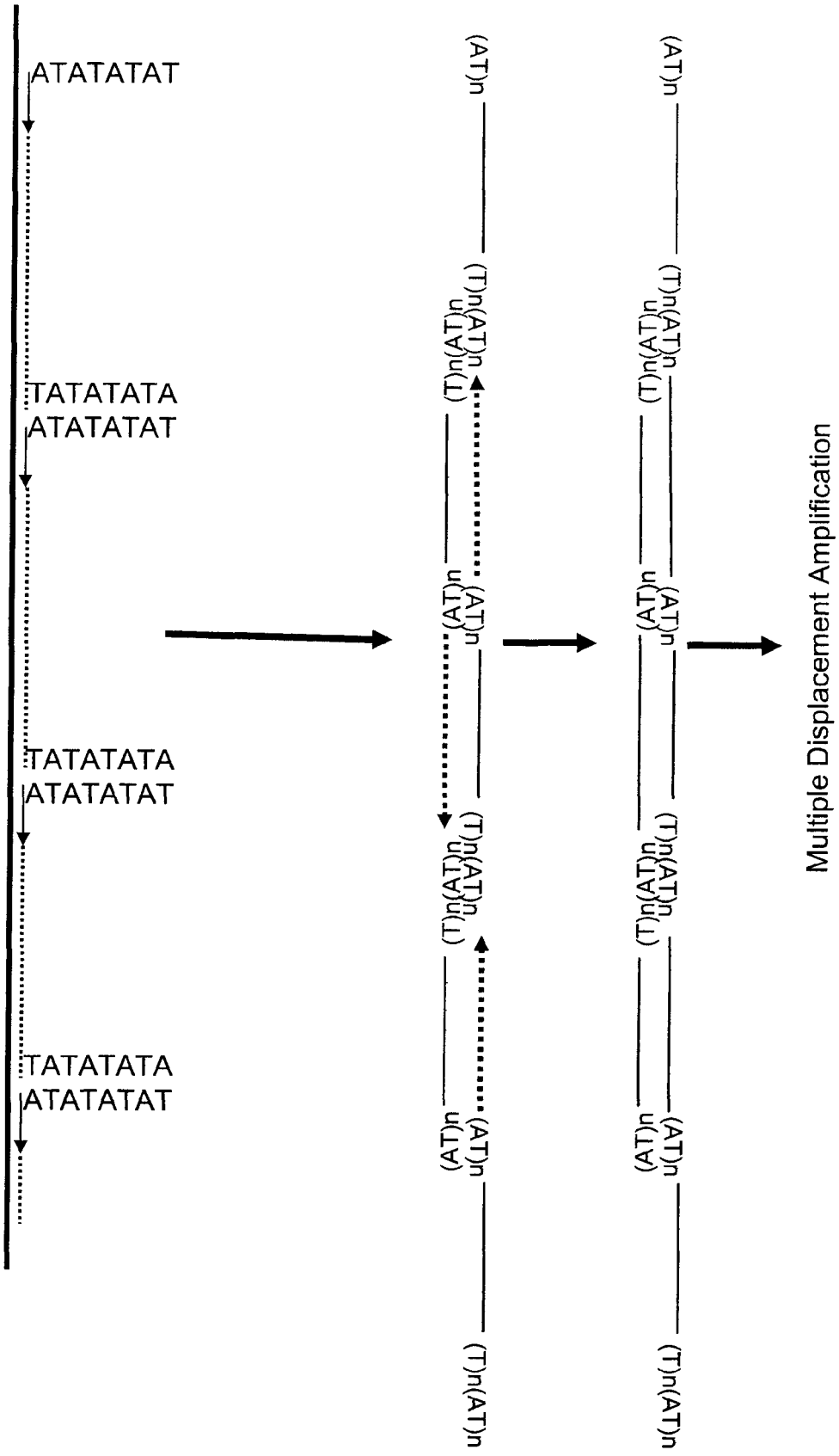
FIG. 14 shows a schematic representation of a method according to the invention in the context of a fusion of nucleic acid molecules, in which a sequence is inserted into the newly synthesized strand complementary to itself by means of the template tag sequence of the anchor oligonucleotide during the synthesis of the new strand of nucleic acid, i.e. that the 3' end of the newly synthesized strand of nucleic acid can hybridize with the 3' of an additional newly synthesized strand. The primer tag sequence is arranged in such a way that the 5' end of the newly synthesized strand of nucleic acid can hybridize with the 5' of an additional newly synthesized strand. In the present case, the template tag sequence of the anchor oligonucleotide and the primer tag sequence are identical $((AT)_n)$. Thus, linear or circular hybridization structures can form. The single-stranded regions are subsequently filled in with a polymerase, and the single-strand nicks are ligated. A subsequent multiple displacement amplification or rolling circle amplification reaction can be used for duplicating the sequences.

This embodiment concerns the anchor oligonucleotides for the fusion of transcriptome or genome fragments. An objective of the present variation in the procedure is to insert fusion sites into the newly synthesized nucleic acid by means of the template tag sequences of the anchor oligonucleotides in order to fuse two or more newly synthesized nucleic acids. This can be carried out, for example, by an evolutive procedure or also SAGE by using DNA or RNA as template nucleic acids. FIG. 14 schematically represents how the template tag sequence of the anchor oligonucleotide is inserted complementary into the newly synthesized strand. Starting from a first oligo-dT primer containing an (AT)n tag, and an anchor oligonucleotide containing an (N)n as an anchor sequence, and, likewise, a (AT)n sequence as a template tag sequence, (AT)n tags are produced at the ends of the newly synthesized nucleic acids that can hybridize with one another. After the ends of two or more newly synthesized strands of nucleic acid hybridize, circular or linear aggregates are formed. In a subsequent polymerase and ligase reaction, the individual molecules are covalently coupled to one another linearly so that fusion molecules are formed.

0.01 µg of total RNA is brought into contact with T4 polymerase, pol buffer, dNTP and 10 µM of anchor oligonucleotide in a polymerase reaction. In this special case, the anchor oligonucleotide also functions as a primer for the polymerase reaction and has inserted the sequence $(AT)_{10}N_8$ (here, the $(AT)_{10}$ sequence is used, as well as a random anchor sequence with n=8). The reaction takes place for 60 minutes at 37° C. Subsequent heating of the reaction mixture at 95° C. for five minutes leads to the denaturing of the DNA and the inactivation of the polymerase. After rehybridization of the DNA molecule, the A-T ends hybridize with each other. With the addition of a DNA polymerase (T4 polymerase), the ends are filled up. Fusioned DNA molecules are formed which are covalently binded to each other in a subsequent ligation reaction with T4 ligase. The resulting large molecules are amplified by MDA (REPLI-g®, QIAGEN).

EXAMPLES

The invention is described in more detail in the following examples.

Example 1

Figure 6:
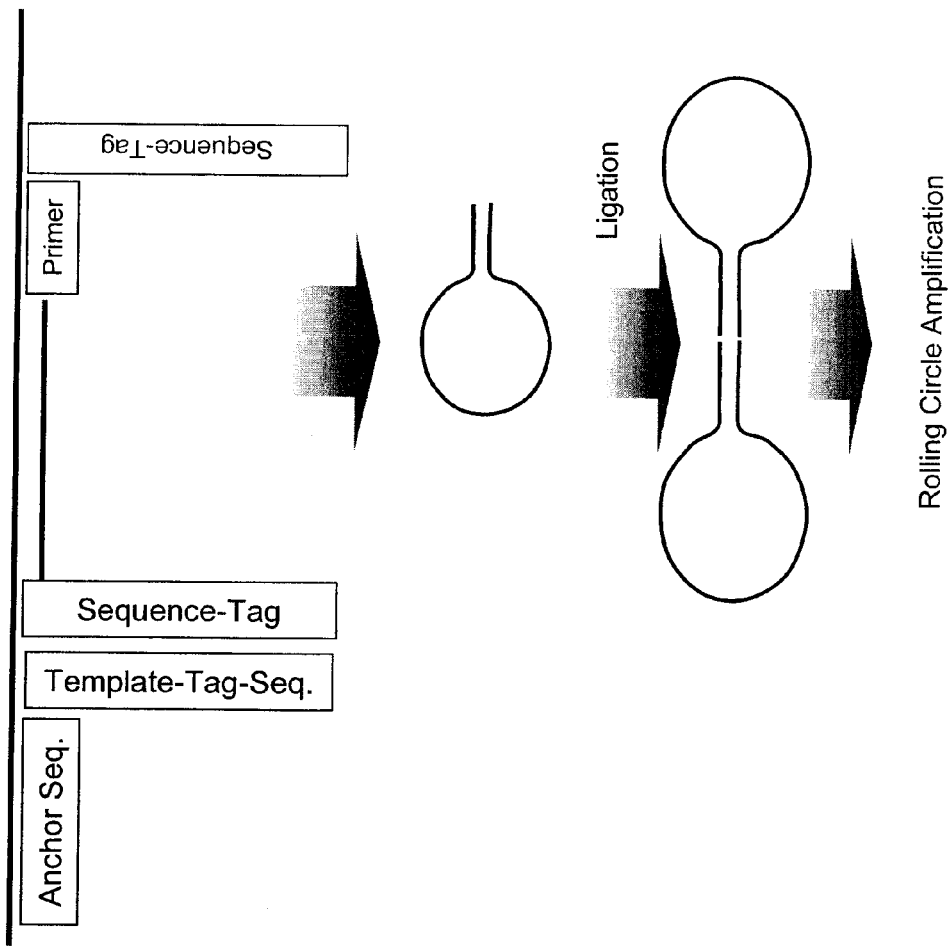
FIG. 6 shows a schematic representation of a DNA amplification, in which during the synthesis of the new strand of nucleic acid starting from RNA or DNA a tag sequence is inserted at the 3' end of the newly synthesized nucleic acid, which is complementary to the primer tag sequence, by means of the template tag sequence of the anchor oligonucleotide, so that intramolecular hairpin loop structures form after the newly synthesized strand of nucleic acid is denatured from the template strand. These can be used for ligation reactions in order to amplify nucleic acids in a subsequent rolling circle amplification reaction.

This example concerns DNA amplification. This embodiment of the amplification according to the invention begins with the same steps as in the RNA amplification corresponding to Embodiment 2. In the present example, a tag sequence was inserted at the 5' end of the newly synthesized nucleic acid by means of a primer with a tag sequence at its 5' end, in addition to the tag sequence that was inserted at the 3' end of the newly synthesized nucleic acid by means of the template tag sequence of the anchor oligonucleotide. The primer tag sequence, as well as the template tag sequence of the anchor oligonucleotide, contained an identical sequence. This led to the tag sequences on the 3' and 5' end of the newly synthesized nucleic acid being complementary to each other. After hybridization of the 3' end of the newly synthesized nucleic acid with the complementary 5' end of the newly synthesized nucleic acid strand, a hairpin structure is formed containing a blunt double-stranded end. Two such hairpin loops were ligated in a "blunt-end" ligation, so that a dumbbell-shaped, circular DNA molecule was formed. This was amplified by RCA (schematic representation in FIG. 6).

Figure 7:
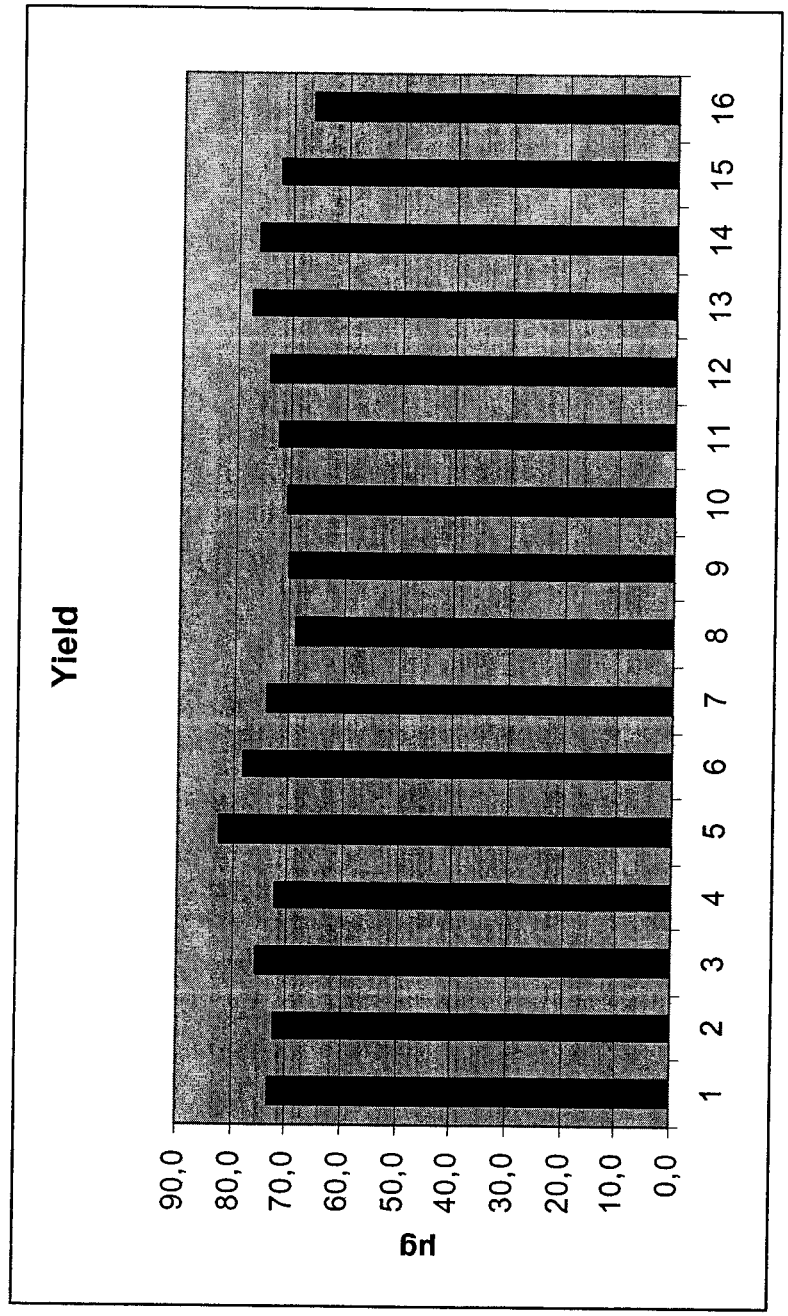
FIG. 7 shows the experimental results from Example 1.

For every 100 ng, RNA was converted into a polymerase reaction with the reverse transcriptase Sensiscript® (QIAGEN) in 16 different experiments. The polymerase reaction was carried out in the presence of a suitable buffer, nucleotides (0.5 mM) and anchor oligonucleotides (10 µM). The template tag sequence of the anchor oligonucleotides contained a specific sequence (here, a T7 RNA polymerase promoter) in the 5' region and 8-mer random sequence in the 3' region. After a reaction time of one hour at 37° C., the reaction mixture was heated at 95° C. for five minutes. The DNA was next ligated using T4 ligase. The resulting ligation products were amplified in an RCA reaction with the REPLI-g® Kit (QIAGEN). In this way the starting amount was strongly amplified to the cDNA; in each case, more than 60 µg DNA were formed (see FIG. 7).

Example 2

In the present example, it is shown that the template tag sequence of the anchor oligonucleotide functions as a template for the synthesis of the 3' end of the newly synthesized strand. The anchor oligonucleotides and primer inserted in this experiment were identical in their sequence. The hybridizing ranges of the anchor oligonucleotide and primer were 8-mer random sequences at the 3' end. The template tag sequence of the anchor oligonucleotides and the primer tag sequence both had the tag7 sequence. A 20 µl reverse transcriptase reaction was carried out in an RT buffer with 100 ng of total RNA, 0.5 mM dNTPs, 100 U Rnase inhibitor (Promega), the Sensiscript® RT Kit (QIAGEN) and 10 µM of anchor oligonucleotides (Operon Biotechnologies Inc.), which also functions as primers. The reaction was carried out for 60 minutes at 37° C. After the reverse transcriptase reaction, the arrangement was divided. One half of the cDNA reaction arrangement was purified with a MinElute Kit (QIAGEN), according to the Cleanup Protocol to remove the anchor oligonucleotides also functioning as primers. The purified DNA was eluted with a volume of 10 µl. In the real-time PCR, the same quantity of purified and unpurified cDNA were amplified and quantified in different reaction vessels.

In this experiment, the anchor oligonucleotides with the sequence:

(SEQ ID NO: 1)
aat tct aat acg act cac tat agg gag aag gnn nnn nnn was used. The real-time PRC was carried out with the primer:

(SEQ ID NO: 5)
aat tct aat acg act cac tat agg

Figure 15:
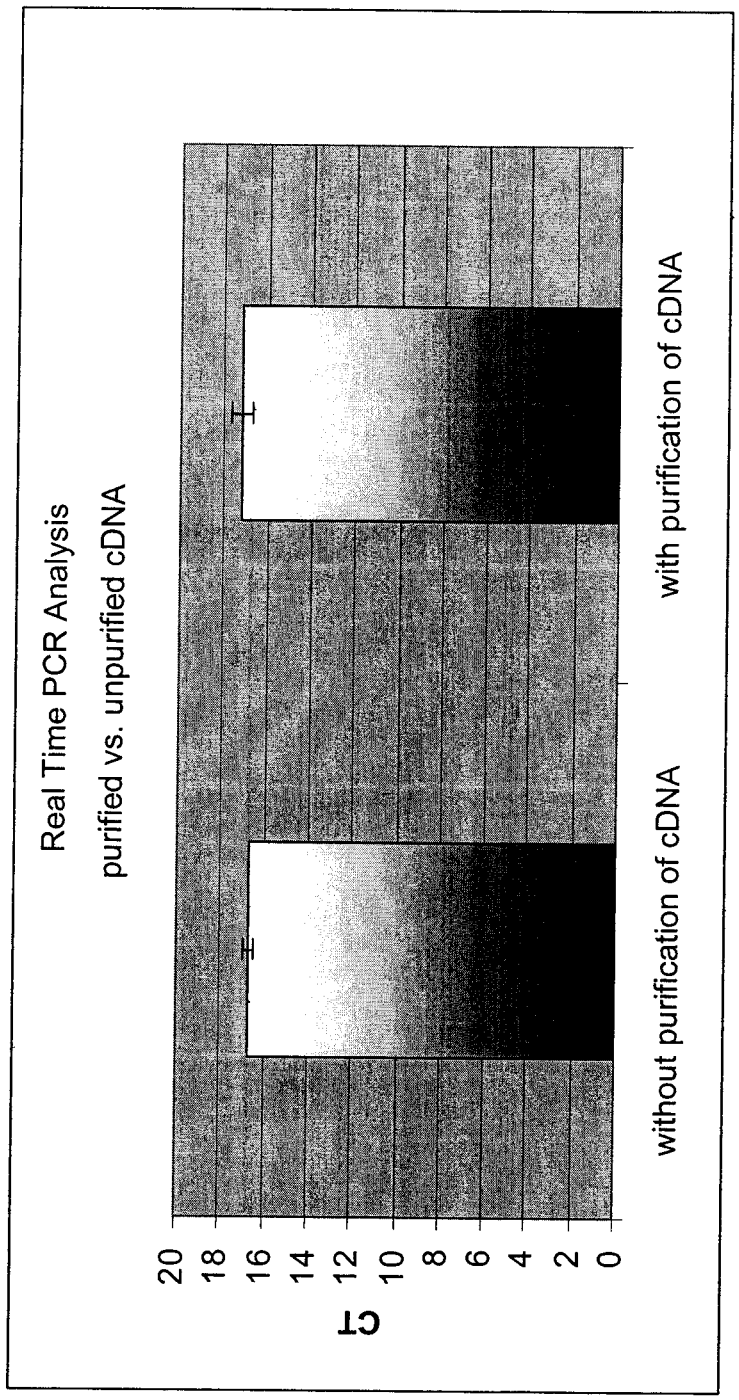
FIG. 15 shows a bar plot of the real-time PCR analysis from Example 2.

The real-time PCR was carried out in an ABI Prism 7700 according to the QuantiTect SYBR Green protocol (QIAGEN). The real-time PCR analysis of the PCR fragments can be seen in FIG. 15. The same CT value could be achieved with both of the newly synthesized strands of nucleic acid (purified or unpurified).

This means that the template tag sequence of the anchor oligonucleotide was not initially inserted during second-strand synthesis (here, carried out during the PCR), since the anchor oligonucleotide was no longer present in the purified probe in the reaction mixture during the PCR as a result of purification. Thus, the tag7 sequence was already inserted by the reverse transcriptase by means of the template switch during the synthesis of the newly synthesized strand.

Example 3

This experiment showed that the tag sequence is inserted at the 3' end of the newly synthesized strand of nucleic acid by means of the template tag sequence of the anchor oligonucleotide, also with the blocked 3' end, i.e. a 3' end not extendable by a polymerase. This means that the template tag sequence functioned as a template by the template switch in the synthesis of the new strand of nucleic acid, and the anchor oligonucleotide was not used as a primer for second-strand synthesis.

A 20-μl reverse transcriptase reaction was carried out with 100 ng of total RNA, 0.5 mM dNTPs, 10 U Rnase inhibitor (Promega), Sensiscript (QIAGEN), 1 μM of β-actin primer (Operon) and 10-μM of anchor oligonucleotides (Operon) according to the Sensiscript standard protocol. The reaction was carried out for 60 minutes at 37° C. The anchor oligonucleotide bore a blocked 3' end (inverse base G=dG-ref-Q), which is not extendable, and, in addition, contained an 8-mer random sequence at the 3' end (anchor sequence) and a template tag sequence (here, the T7P sequence) at the 5' end.

T7P-N8 block:
(SEQ ID NO: 21)
AATTCTAATACGACTCACTA TAGGGAGAAGGNNNNNNNN-dG-ref-Q

T7P-N8:
(SEQ ID NO: 22)
CAATTCTAATACGACTCACTA TAGGGAGAAGGNNNNNNNNG

T7P:
(SEQ ID NO: 10)
AATTCTAATACGACTCACTA TAGGGAGAAGG

β-actin:
(SEQ ID NO: 11)
GTCTCAAGTCAGTGTACAGG

Figure 16:
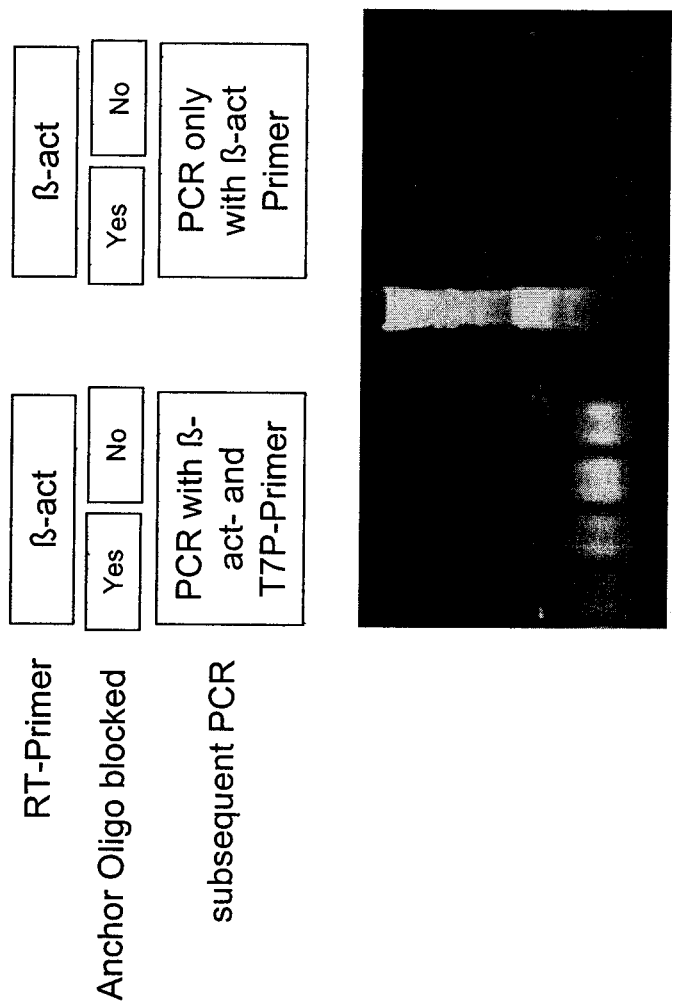
FIG. 16 shows a gel analysis of the amplificate from Example 3.

In comparison, the same experiment was carried out with an unblocked anchor oligonucleotide with an otherwise identical sequence. The cDNA produced in the RT reaction was amplified in different PCRs, whereby (a) β-actin and T7 primer or (b) only β-actin primer were supplied. The PCR followed the standard protocol for an endpoint PCR according to the Taq PCR Handbook from QIAGEN. The gel analysis of the PCR fragments can be seen in FIG. 16. A kb ladder (1 kb ladder, Invitrogen GmbH) was used as a label. cDNA amplificates were only recognizable in a size of 350 bp, when both primers (β-actin and T7P primer) were used in the PCR. Thus, whether the cDNA synthesis was carried out with blocked or unblocked anchor oligonucleotides did not play a role; cDNA amplificates were obtained with both anchor oligonucleotides (blocked/unblocked 3' end). However, no amplificates were produced when the PCR was carried out with only β-actin primers.

This means that the tag sequence was already inserted into the newly synthesized nucleic acid during first-strand cDNA synthesis with the reverse transcriptase by means of the template switch instead of during second-strand synthesis by extension of the anchor oligonucleotide, since a free 3'-OH end at the anchor oligonucleotide, which would have been required for corresponding second-strand synthesis, was not necessary.

Example 4

This example illustrated that anchor sequences of different lengths at the 3' end of the anchor oligonucleotide can hybridize to the template nucleic acid with varying degrees of efficiency.

A reverse transcriptase reaction was carried out with 100 ng of total RNA or 0 ng of total RNA (negative control), 0.5 mM dNTPs, 10 U Rnase inhibitor (Promega), 4 U Omniscript RT (QIAGEN) and 10 μM of anchor oligonucleotides (Operon). In the present experiment, the anchor oligonucleotides at the same time functioned as primers. The reaction was carried out for 60 minutes at 37° C. The anchor nucleotides bore a free 3'-OH end and further contained a random sequence of 8 or more bases at the 3' end (anchor sequence) and a template tag sequence (T7).

Different anchor oligonucleotides with anchor sequences of various lengths ($N_8$, $N_{10}$, $N_{12}$, whereby N=A,C,G, or T) were used. The newly synthesized nucleic acid was amplified in a PCR with primers containing only the T7 sequence. The PCR followed a standard protocol for an endpoint PCR according to the Taq PCR Handbook from QIAGEN. In a further PCR, the same newly synthesized nucleic acid was amplified with primers that specifically recognize the β-actin transcriptase. The following oligonucleotides were used:

T7:
(SEQ ID NO: 12)
gga tga cga cgc agt att g

β-actin primer:
(SEQ ID NO: 11)
gtctcaagtcagtgtacagg
(SEQ ID NO: 18)
gtga tagcattgctttcgtg T7N8:
(SEQ ID NO: 2)
gga tga cga cgc agt att g nnn nnn nn T7N10:
(SEQ ID NO: 3)
gga tga cga cgc agt att g nnn nnn nnn n

```
T7N12:
                                               (SEQ ID NO: 4)
gga tga cga cgc agt att g nnn nnn nnn nnn
```

Figure 17:
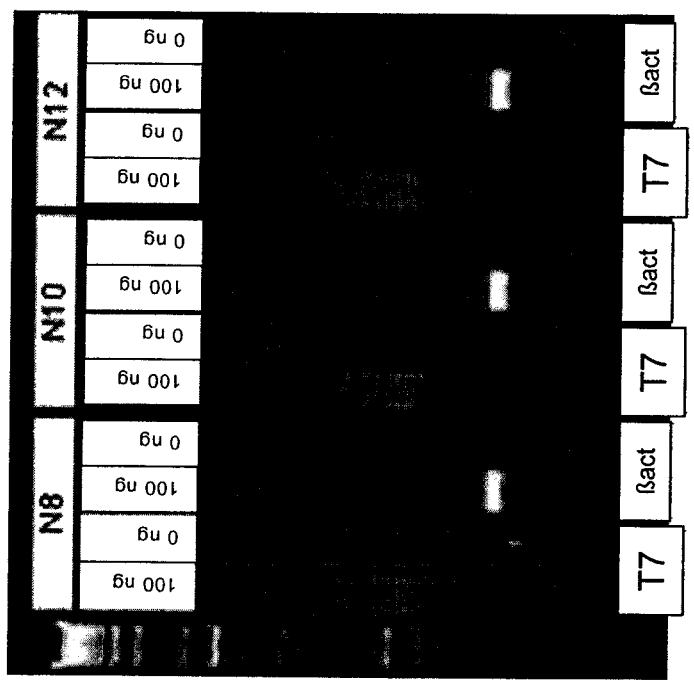
FIG. 17 shows a gel analysis of the amplificate from Example 4.

The gel analysis of the PCR fragments can be seen in FIG. 17. The 1 kb ladder (see Example 3) was used as a large marker. In the negative control, no amplificates were recognized, since no RNA was present during the reverse transcriptase reaction. The amplification with T7 primers led to varyingly large fragments having sizes of 200 bp up to 1500 bp, whereby both the size and the quantity became larger if the length of the anchor sequence increased. A fragment of nucleic acid of the expected size was amplified with the β-actin primer.

Consequently, it can be concluded that anchor oligonucleotides can be used as such as well as concomitantly as primer in order to introduce the tag sequence at the 3' end of the newly synthesized nucleic acid, as well as at the 5' end. Furthermore, the longer the random anchor sequence is, the less frequently these specifically hybridize with the template nucleic acid, since the statistical frequency of each respective sequence decreases in the crowd of the random anchor sequences of the anchor oligonucleotides. Moreover, however, a longer random anchor sequence also hybridizes more efficiently with the template nucleic acid. This becomes visible with the quantity and length of the amplificates, which were obtained by a PCR with primers of the T7 sequence (FIG. 17).

Example 5

This example illustrates that various reverse transcriptases facilitate the attachment of tag sequences at the 3' end of the newly synthesized nucleic acid by means of the template tag sequences of anchor oligonucleotides by the template switch.

Reverse transcriptase reactions were carried out with 100 ng of total RNA or 1 ng of total RNA, 0.5 mM dNTPs, 10 U Rnase inhibitor (Promega), various reverse transcriptases and 10 µM of anchor oligonucleotides (Operon). In the present experiment, the anchor oligonucleotides (T7 N6 T4) also function concomitantly as primers. The reaction was carried out for 60 minutes at 37° C. The anchor nucleotides bore a free 3'-OH end and further contained an 8-mer random sequence followed by 4 T at the 3' end (anchor sequence, and a template tag sequence (T7).

Figure 18:
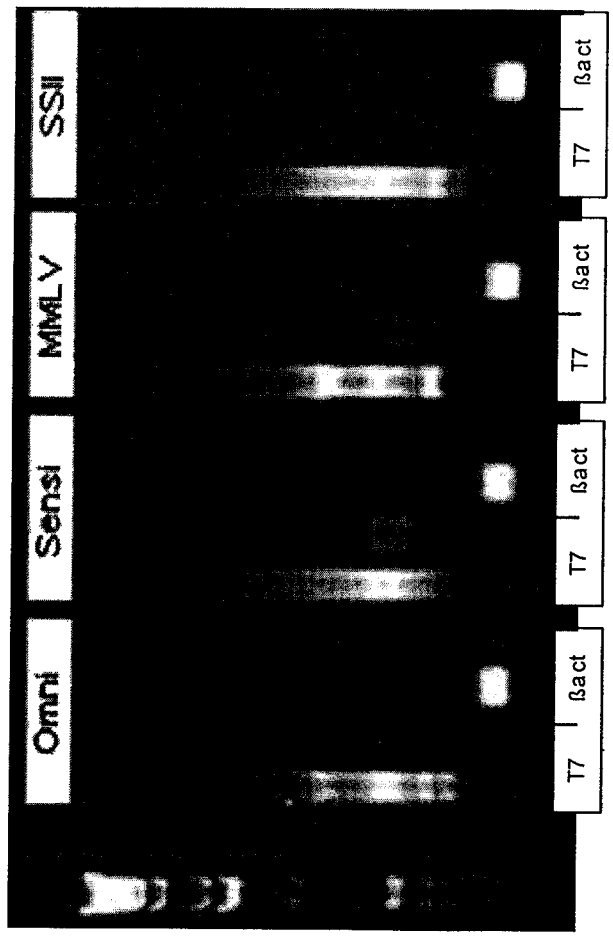
FIG. 18 shows a gel analysis from Example 5.

Omniscript (QIAGEN), Sensiscript (QIAGEN), MMLV RT (Invitrogen) or MMLV RT without RNase H activity (Superscript II, abbreviated SSII in FIG. 18; each reaction carried out.

The newly synthesized nucleic acid was amplified in a PCR with primers containing only the T7 sequence. The PCR followed a standard protocol for an endpoint PCR according to the Taq PCR Handbook from QIAGEN. In a further PCR, the same newly synthesized nucleic acid was amplified with primers specifically recognizing the β-actin transcript. The following oligonucleotides were used:

```
T7:
gga tta cga ctc agt att g                      (SEQ ID NO: 15)

T7 N6 T4:
gga tta cga ctc agt att g nnnnnn              (SEQ ID NO: 16)
tttt

β-actin primer:
gtctcaagtcagtgtacagg                           (SEQ ID NO: 11)

gtga tagcattgctttcgtg                          (SEQ ID NO: 18)
```

The gel analysis of the PCR fragments can be seen in FIG. 18. The 1 kb ladder (see Example 3) was used as a large marker. Amplification with T7 primers led to various large fragments having sizes of approximately 300 to 2500 bp. A fragment of the expected size was amplified with the β-actin primers. In first-strand cDNA, the tag sequence could be successfully inserted with all reverse transcriptase.

It can be concluded that various reverse transcriptases can introduce the insertion of the tag sequences into the newly synthesized nucleic acids via the template tag sequence of the anchor oligonucleotides.

Example 6

It is shown in this example that the distance between the anchor oligonucleotide's hybridization sites can be modulated. Thus, the template tag sequences of the anchor oligonucleotides were used for inserting the tag sequence into the newly synthesized strand of nucleic acid.

A reverse transcriptase reaction was carried out with 0 ng (negative control), 1 ng or 100 ng of total RNA, 0.5 mM dNTPs, 10 U Rnase inhibitor, 4 U Omniscript® (QIAGEN) and various anchor oligonucleotides (in each case 10 µM). In this special case, the anchor oligonucleotides also served as primers. The reaction was carried out for 30 minutes at 37° C. Each anchor nucleotide bore a free 3'-OH end and had a 6-mer random anchor sequence located between the $T_n$ sequence (with n=0, 1, 2 or 3) at the 3' end and a template tag sequence (designated T7 here) at the 5' end. The primers differed in the length of the oligo-T region at the 3' end located between 0 and 3 (T0, T1, T2, T3).

The newly synthesized strand of nucleic acid was amplified in a PCR with primers that hybridized with the T7 sequence. The PCR followed a standard protocol for an endpoint PCR according to the Taq PCR Handbook from QIAGEN. In a further PCR, the same newly synthesized strand of nucleic acid was amplified with primers that specifically recognize the β-actin transcript. The following oligonucleotides were used:

```
T7:
gga tga cga cgc agt att g                      (SEQ ID NO: 12)

T3:
gga tga cga cgc agt att g nnnnnn              (SEQ ID NO: 9)
ttt

T2:
gga tga cga cgc agt att g nnnnnn              (SEQ ID NO: 8)
tt

T1:
gga tga cga cgc agt att g nnnnnn t            (SEQ ID NO: 7)

T0:
gga tga cga cgc agt att g nnnnnn              (SEQ ID NO: 6)

β-actin primer:
gtctcaagtcagtgtacagg                           (SEQ ID NO: 11)

gtga tagcattgctttcgtg                          (SEQ ID NO: 18)
```

Figure 19:
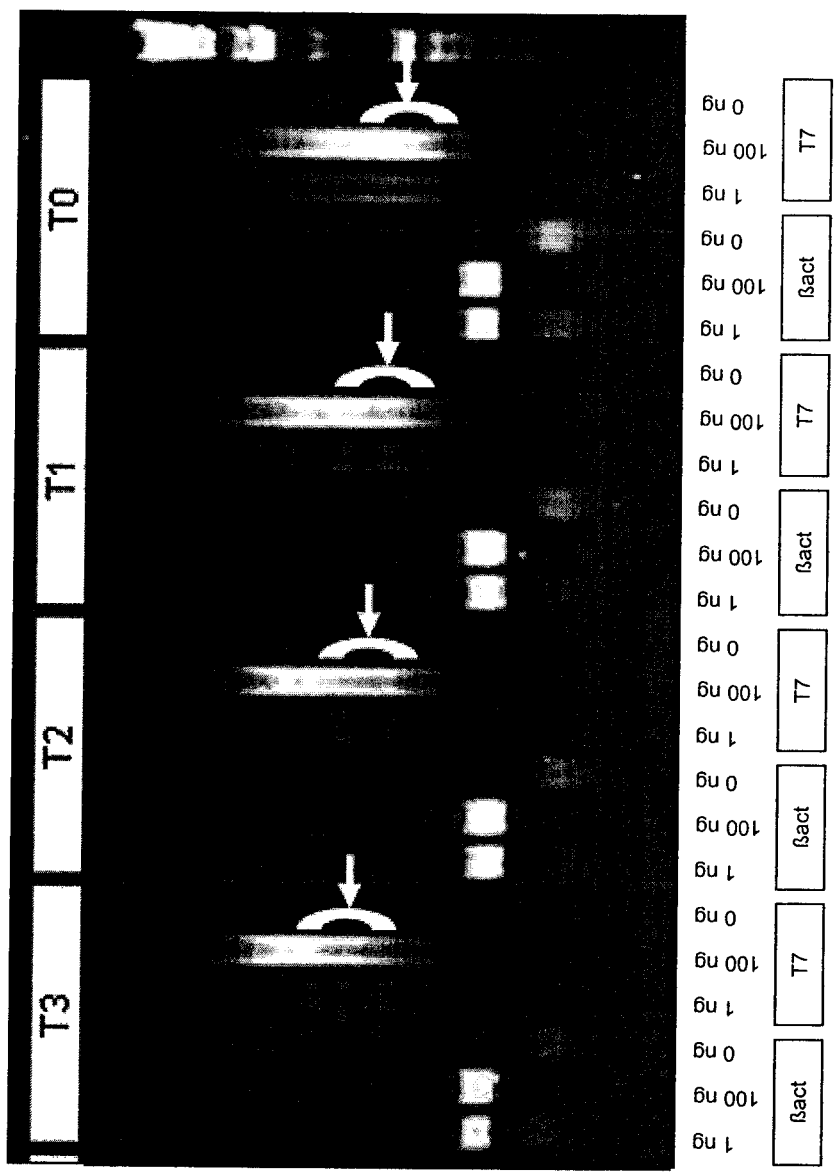
FIG. 19 shows a gel analysis from Example 6.

The gel analysis of the PCR fragments can be seen in FIG. 19. The 1 kb ladder (see Example 3) was used as a marker. Amplification with T7 primers led to a crowd of various large fragments having a size of approximately 300 to 2500 bp. A fragment of the expected, definite size was amplified with the β-actin primers. With all the anchor oligonucleotides used in this example, the tag sequence could be successfully inserted into the newly synthesized strand of nucleic acid by means of the template tag sequences. This is evident from the successful amplification of the newly synthesized strands of nucleic acid with primers which hybridize to the tag sequence (see FIG. 19). These amplificates, on average, became larger by increasing the specificity of the anchor sequence by increasing the number of thymine bases at the 3' end of the anchor oligonucleotide. In addition, with the increase in specificity, the amount on the primer dimmer products decreased (in FIG. 19, see the reaction products in the solution '0 ng,' which contain no RNA in the RT reaction).

Thus, it can be concluded that increasing the specificity of the anchor sequence increases the distance of the hybridization of the anchor oligonucleotides. Also, the amount on the unspecified primer dimer product is reduced with the increase of the specificity of the anchor sequence.

Example 7

On the basis of this example, the efficiency of the insertion of the tag sequence by means of the template tag sequence of anchor oligonucleotides was examined in a real-time PCR. Thus, the template tag sequences of anchor oligonucleotides were used for inserting a tag sequence into the newly synthesized strand of nucleic acid.

A reverse transcriptase reaction was carried out with 100 ng of total RNA, 0.5 mM dNTPs, 10 U Rnase inhibitor (Promega), Sensiscript® (QIAGEN) and different anchor nucleotides (10 µM in each case), primers (Operon) according to the Sensiscript Kit Handbook (QIAGEN). The reaction took place for 30 minutes at 37° C.

In each case, all of the anchor oligonucleotides bore a free 3'-OH end and further contained a random sequence as an anchor sequence in the 3' region and a template tag sequence (gga tga cga cgc agt att g) in the 5' region. The newly synthesized nucleic acid was amplified and quantified in a real-time PCR. Oligonucleotides which hybridize to the tag sequence were inserted as primers in this case. The following oligonucleotides were used:

```
T7:
gga tga cga cgc agt att g            (SEQ ID NO: 12)

N8:
gga tga cga cgc agt att g nnn nnn    (SEQ ID NO: 2)
nn

N10:
gga tga cga cgc agt att g nnn nnn    (SEQ ID NO: 3)
nnn n

N12:
gga tga cga cgc agt att g nnn nnn    (SEQ ID NO: 4)
nnn nnn

G2 N6:
gga tga cga cgc agt att ggg nnn      (SEQ ID NO: 13)
nnn

G4 N6:
gga tga cga cgc agt att ggg gg nnn   (SEQ ID NO: 14)
nnn
```

Figure 20:
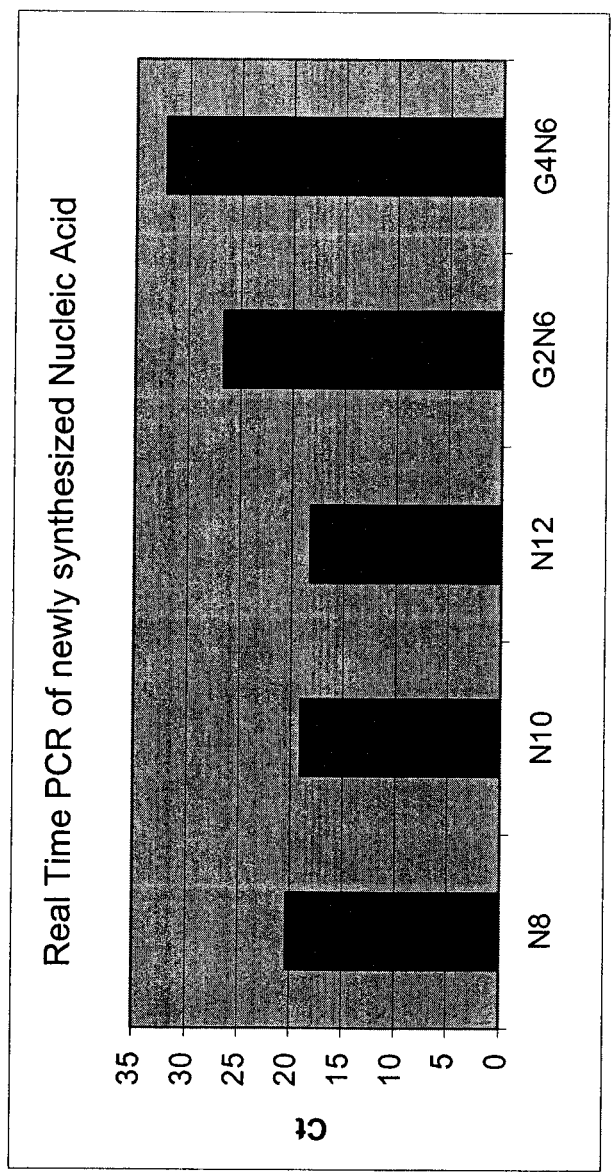
FIG. 20 shows a bar plot with the result of real-time amplification from Example 7.

The real-time PCR analysis of the PCR fragments can be seen in FIG. 20. The real-time PCR followed the protocol of the QuantiTect SYBR Green Kit from QIAGEN. The tag sequence could be successfully inserted into the newly synthesized strand of nucleic acid with all of the anchor oligonucleotides. The resulting strands of newly synthesized strands of nucleic acid could then be successfully analyzed in the real-time PCR with primers which hybridized on the tag sequence of the newly synthesized nucleic acid.

From this it can be recognized that the efficiency of the insertion of the tag sequence into the newly synthesized strand of nucleic acid can be quantified by a real-time PCR. In this special experiment, extending the random anchor sequence to 12 bases led to an improved efficiency of the insertion (see FIG. 20, primer N12).

Example 8

The example has shown that whole genome amplification can be carried out by the method according to the invention. In this connection, gDNA functions as the template nucleic acid. In this example, tag sequences were also inserted into the newly synthesized strand of nucleic acid in a polymerase reaction by means of the template tag sequences of the anchor oligonucleotides.

The anchor oligonucleotide T7P N8 was used as an anchor oligonucleotide. The anchor oligonucleotide contains a T7 promoter sequence at the 5' end as a template tag sequence. The 3' region contained an 8-mer random sequence.

Initially, 120 ng of gDNA from HeLa cells was denatured in the presence of T7P N8 oligonucleotide (10 µM), reaction buffer and dNTPs (0.5 mM) at 95° C. for 5 minutes. Alternatively, a blocked (i.e. with a 3' end not extendable with a polymerase) anchor oligonucleotide with the same sequence (T7P N8 block) was inserted in place of the T7P N8 oligonucleotide. In another alternative, an 8-mer random primer can also be used.

```
T7P N8:
                                         (SEQ ID NO: 19)
CAA TTC TAA TAC GAC TCA CTA TAG GGA GAA GGN NNN
NNN N

T7P N8 block:
                                         (SEQ ID NO: 23)
CAA TTC TAA TAC GAC TCA CTA TAG GGA GAA GGN NNN
NNN N -dG-ref Q.

N8:
                                         (SEQ ID NO: 17)
NNN NNN NN
``` dG-ref Q is an inversely oriented guanine base that cannot be extended via a polymerase.

After denaturing the DNA, the reagent mixture was cooled to room temperature. 4 U MMLV (RNase H minus) (SuperscriptII, Invitrogen) were then added, and the solutions were incubated for one hour at 37° C. 1 µl of the reaction mixture was transferred to a PCR which was carried out in 40 cycles in a 20 µl solution with a primer that can hybridize with the tag sequence of the newly synthesized strand of nucleic acid (here, primer T7P), dNTPs, PCR buffer and taq polymerase.

```
                                         (SEQ ID NO: 20)
T7P:   CAA TTC TAA TAC GAC TCA CTA TAG GGA GAA GG
```

Figure 21:
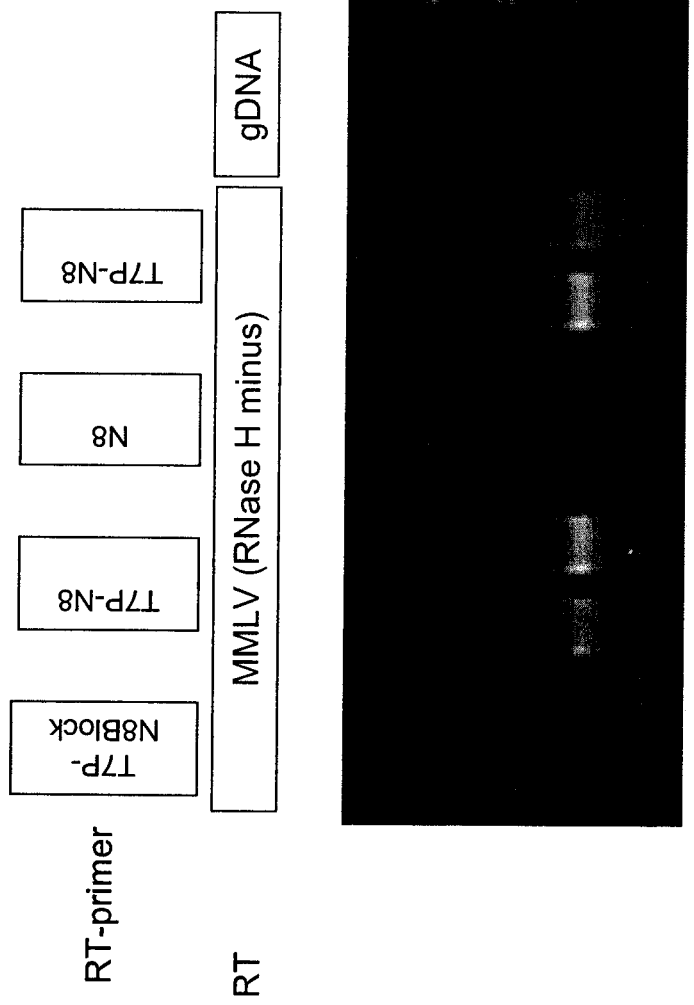
FIG. 21 shows a gel analysis from Example 8.

The results of this experiment indicate that an insertion of the tag sequence by means of an anchor oligonucleotide was possible, namely, if DNA was used as a template. Whole genome amplification is, therefore, possible, in the method according to the invention. Insertion of the tag sequence into the newly synthesized nucleic acid was not possible if an anchor oligonucleotide with a blocked 3' end is used, since, in this case, the anchor oligonucleotide likewise functions as a primer during the polymerase reaction (see FIG. 21).

Example 9

This example showed that, in addition to reverse transcriptases, other polymerases could facilitate the insertion of the tag sequence into the newly synthesized strand of nucleic acid by means the template tag sequence of the anchor oligonucleotide.

For this, the anchor oligonucleotide T7P N8 was used (sequence: CAA TTC TAA TAC GAC TCA CTA TAG GGA GAA GGN NNN NNN N) (SEQ ID NO: 19). Initially, 10 ng of gDNA from HeLa cells were denatured with T7P N8 oligonucleotide (10 µM), 1× Klenow buffer and dNTPs (0.5 mM) at 95° C. for 5 minutes. Alternatively, an N8 primer (sequence: NNN NNN NN (SEQ ID NO: 17)) was used. The denatured reagent mixture was cooled to room temperature. 1 µl Sensiscript (QIAGEN), 12 U AMV reverse transcriptase or 10 U Klenow fragment of DNA polymerase I from E. coli was then added to the individual solutions and incubated for one hour at 37° C. Subsequently, 1 µl of the reaction mixture was transferred to a PCR which was carried out in 40 cycles in a 20 µl solution with a T7P primer (sequence: CAA TTC TAA TAC GAC TCA CTA TAG GGA GAA GG (SEQ ID NO: 20)), dNTPs, primer, PCR buffer and taq polymerase.

Figure 22:
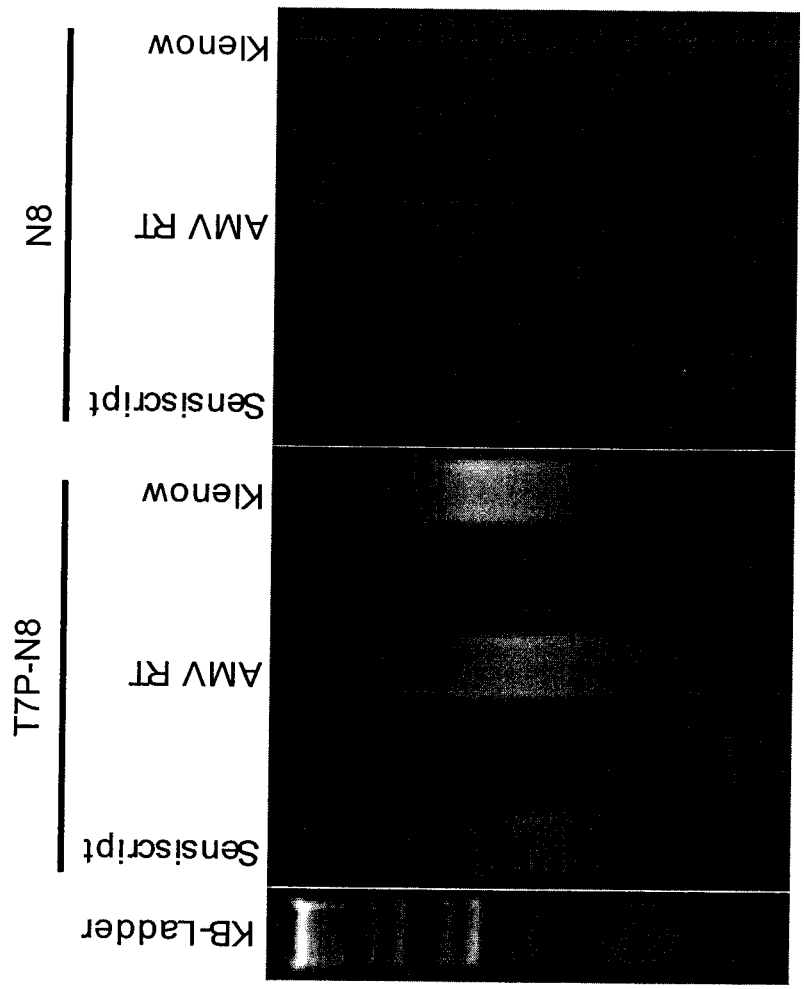
FIG. 22 shows a gel analysis from Example 9.

The results of the experiment (see FIG. 22) in this example show that other polymerases, in this case the Klenow fragment of the DNA polymerase I, can facilitate the insertion of a tag sequence into the newly synthesized strand of nucleic acid by means of the template tag sequence of an anchor oligonucleotide.

What is claimed is:

1. A method for random insertion of a tag sequence into a nucleic acid comprising:
in a first strand synthesis reaction,
(a) providing a template nucleic acid and a primer,
(b) hybridizing an anchor oligonucleotide to the template nucleic acid,
wherein the anchor oligonucleotide comprises an anchor sequence and a template tag sequence,
wherein the anchor sequence is a random sequence, and
wherein the template tag sequence is a non-hybridized portion of the anchor oligonucleotide; and
(c) extending the primer of step (a), along the template nucleic acid to form a new strand of nucleic acid,
wherein a portion of the new strand of nucleic acid comprises a sequence complementary to the template nucleic acid, and
wherein a portion of the resulting new strand of nucleic acid comprises a sequence complementary to the template tag sequence of the anchor oligonucleotide thereby randomly inserting a sequence complementary to the template tag sequence of the anchor oligonucleotide into a new strand of nucleic acid.

2. The method of claim 1, wherein the anchor sequence of the anchor oligonucleotide is located at the 3' region and the template tag sequence of the anchor oligonucleotide is located in the 5' region of the anchor oligonucleotide.

3. The method of claim 1, characterized in that the template tag sequence contains at least one functional sequence.

4. The method of claim 2, characterized in that the template tag sequence contains at least one functional sequence.

5. The method of claim 1, wherein a polymerase with slight or no strand displacement activity is used in Step (c).

6. The method of claim 2, wherein a polymerase with slight or no strand displacement activity is used in Step (c).

7. The method of claim 3, wherein a polymerase with slight or no strand displacement activity is used in Step (c).

8. The method of claim 1, wherein the method for random insertion of a tag sequence into a nucleic acid functions for the synthesis of RNA.

9. The method of claim 1, wherein the method for inserting random insertion of a tag sequence into a nucleic acid serves for the synthesis of DNA.

10. The method of claim 1, wherein the method for random insertion of a tag sequence into a nucleic acid is used for detecting template nucleic acids.

11. The method of claim 1, wherein the method for random insertion of a tag sequence into a nucleic acid is used for fusing DNA fragments.

12. The method of claim 1, wherein methylated DNA sections are selectively amplified.

13. The method of claim 1, wherein non-methylated DNA sections are selectively amplified.

14. The method of claim 1, wherein the tag sequence is inserted without subsequent synthesis of the opposite strand at the 3' end of the newly synthesized nucleic acid.

15. The method of claim 1, further comprising detecting the new strand of nucleic acid produced in step (c).

16. The method of claim 1, further comprising amplifying the new strand of nucleic acid produced in step (c).

17. The method of claim 1, wherein the anchor sequence of the anchor oligonucleotide is a primer.

18. The method of claim 3, wherein the at least one functional sequence is a hybridization site, a primer binding site, a probe binding site, a promoter, a signal sequence for initiating transcription and/or translation, a restriction endonuclease recognition and restriction site, a ribosome binding site, a protein binding site, an antibody recognition site, or a sequence complementary thereto.

19. The method of claim 18, wherein the promoter is an RNA polymerase promoter.

20. The method of claim 19, wherein an in vitro transcription reaction is subsequently performed.

21. The method of claim 1, wherein the new strand of nucleic acid is processed by means of a sequence-specific endonuclease.

22. The method of claim 21, wherein the sequence-specific endonuclease is a methylation-sensitive endonuclease.

23. The method of claim 1, wherein more than one primer is used in step (a), wherein the one or more primers comprises a tag sequence.

24. The method of claim 1, wherein a double-stranded region of nucleic acid is formed between the new strand of nucleic acid and the non-hybridized portion of the anchor oligonucleotide, wherein the double-stranded region does not exist prior to the formation of the new strand.

25. The method of claim 24, wherein the double-stranded region of nucleic acid is further processed in a subsequent step (d).

26. The method of claim 25, wherein the anchor sequence of the anchor oligonucleotide is located at the 3' region and at least one template tag sequence of at least one anchor oligonucleotide is located in the 5' region of at least the anchor oligonucleotide.

27. The method of claim 25, characterized in that the template tag sequence contains at least one functional sequence.

28. The method of claim 25, wherein a polymerase with slight or no strand displacement activity is used in Step (c).

29. The method of claim 24, wherein the double-stranded region of nucleic acid is formed by means of a template switch.

30. The method of claim 23, wherein the sequence of the tag sequence of the primer and the sequence of the template tag sequence of the anchor oligonucleotide are identical.

31. The method of claim 23, wherein the sequence of the tag sequence of the primer and the sequence of the template tag sequence of the anchor oligonucleotide are different.

32. The method of claim 27, wherein the at least one functional sequence is a hybridization site, a primer binding site, a probe binding site, a promoter, a signal sequence for initiating transcription and/or translation, a restriction endonuclease recognition and restriction site, a ribosome binding site, a protein binding site, an antibody recognition site, or a sequence complementary thereto.

33. The method of claim 32, wherein the promoter is an RNA polymerase promoter.

34. The method of claim 33, wherein an in vitro transcription reaction is subsequently performed.

35. The method of claim 25, wherein the further processing of step (d) comprises:
  (i) ligating the ends of double-stranded nucleic acid strand synthesized in step (c) without prior strand separation, and subsequently
  (ii) separating the double-stranded nucleic acid, thereby producing circular single-stranded nucleic acids.

36. The method of claim 32, wherein the circular single-stranded nucleic acids are amplified by rolling circle amplification.

37. The method of claim 25, wherein the further processing of step (d) comprises:
  (i) separating the new nucleic acid strand from the template strand, and
  (ii) forming a hairpin structure through self-hybridization of the ends of the newly synthesized nucleic acid strand.

38. The method of claim 37, wherein two hairpin structures are ligated to one another to generate a circular nucleic acid.

39. The method of claim 38, wherein the circular nucleic acid is amplified by rolling circle amplification.

* * * * *